(12) United States Patent
Boudet

(10) Patent No.: US 12,275,937 B2
(45) Date of Patent: Apr. 15, 2025

(54) STEREOSPECIFIC LINKAGES IN RNA EDITING OLIGONUCLEOTIDES

(71) Applicant: ProQR Therapeutics II B.V., Leiden (NL)

(72) Inventor: Julien Auguste Germain Boudet, Leiden (NL)

(73) Assignee: ProQR Therapeutics II B.V., Leiden (NL)

(*) Notice: Subject to any disclaimer, the term of this patent is extended or adjusted under 35 U.S.C. 154(b) by 1034 days.

(21) Appl. No.: 17/054,983

(22) PCT Filed: May 13, 2019

(86) PCT No.: PCT/EP2019/062163
§ 371 (c)(1),
(2) Date: Nov. 12, 2020

(87) PCT Pub. No.: WO2019/219581
PCT Pub. Date: Nov. 21, 2019

(65) Prior Publication Data
US 2021/0230590 A1    Jul. 29, 2021

(30) Foreign Application Priority Data

May 18, 2018   (GB) ..................................... 1808146

(51) Int. Cl.
C12N 15/113    (2010.01)
A61P 3/00      (2006.01)
(52) U.S. Cl.
CPC .............. *C12N 15/113* (2013.01); *A61P 3/00* (2018.01); *C12N 2310/11* (2013.01);
(Continued)

(58) Field of Classification Search
CPC .............. C12N 15/113; C12N 2310/11; C12N 2310/315; C12N 2320/34; C12N 2320/50; A61P 3/00
See application file for complete search history.

(56) References Cited

U.S. PATENT DOCUMENTS 6,531,456 B1    3/2003  Kurtzman et al.
8,053,212 B1    11/2011 Benner
(Continued)

FOREIGN PATENT DOCUMENTS

DE    102015012522 B3    6/2016
EP        1619249 B1     9/2008
(Continued)

OTHER PUBLICATIONS

Rees and Liu, Base editing: precision chemistry on the genome and transcriptome of living cells, 2018, Nat. Rev. Genet., 19, p. 1-41 (Year: 2018).*

(Continued)

*Primary Examiner* — Richard A Schnizer
*Assistant Examiner* — Keyur A Vyas
(74) *Attorney, Agent, or Firm* — Sterne, Kessler, Goldstein & Fox P.L.L.C.

(57) ABSTRACT

The invention relates to editing oligonucleotides (EONs) that carry stereospecific phosphorothioate internucleotide linkage modifications at specified positions and that do not carry such modifications on positions that would lower RNA editing efficiency. The selection of positions that should or should not carry a phosphorothioate Rp and/or Sp configuration modification is based on computational modelling that revealed incompatibilities of the stereospecific linkages with the intermolecular oxygen-mediated hydrogen bond network.

14 Claims, 3 Drawing Sheets

Specification includes a Sequence Listing.

(52) U.S. Cl.
CPC .... *C12N 2310/315* (2013.01); *C12N 2320/34* (2013.01); *C12N 2320/50* (2013.01)

(56) References Cited

U.S. PATENT DOCUMENTS

| | | | |
|---|---|---|---|
| 8,372,816 | B2 | 2/2013 | Brown |
| 8,389,703 | B1 | 3/2013 | Benner et al. |
| 8,507,663 | B2 | 8/2013 | Defougerolles et al. |
| 9,650,627 | B1 | 5/2017 | Rosenthal et al. |
| 9,732,347 | B2 | 8/2017 | Brown et al. |
| 10,676,737 | B2 | 6/2020 | Klein et al. |
| 10,941,402 | B2 | 3/2021 | Turunen et al. |
| 10,988,763 | B2 * | 4/2021 | Turunen ............... C12N 15/111 |
| 11,274,300 | B2 | 3/2022 | Aalto et al. |
| 11,390,865 | B2 | 7/2022 | Fukuda et al. |
| 11,649,454 | B2 | 5/2023 | Turunen et al. |
| 11,781,134 | B2 | 10/2023 | Klein et al. |
| 11,851,656 | B2 * | 12/2023 | Turunen ................ A61P 25/28 |
| 2014/0228556 | A1 | 8/2014 | Fukuda et al. |
| 2014/0357856 | A1 | 12/2014 | Monia et al. |
| 2017/0355985 | A1 | 12/2017 | Dellinger et al. |
| 2018/0028554 | A1 | 2/2018 | Van Deutekom et al. |
| 2018/0208924 | A1 | 7/2018 | Fukuda et al. |
| 2019/0040383 | A1 | 2/2019 | Klein et al. |
| 2019/0093098 | A1 | 3/2019 | Stafforst et al. |
| 2019/0218552 | A1 | 7/2019 | Turunen et al. |
| 2019/0330622 | A1 | 10/2019 | Turunen et al. |
| 2019/0352641 | A1 | 11/2019 | Aalto et al. |
| 2020/0199586 | A1 | 6/2020 | Klein et al. |
| 2021/0079393 | A1 | 3/2021 | Boudet et al. |
| 2021/0238597 | A1 | 8/2021 | Turunen et al. |
| 2021/0340529 | A1 | 11/2021 | Turunen et al. |
| 2022/0127609 | A1 | 4/2022 | Boudet et al. |
| 2022/0177894 | A1 | 6/2022 | Yilmaz-Elis et al. |
| 2022/0307023 | A1 | 9/2022 | Turunen et al. |
| 2022/0307027 | A1 | 9/2022 | Fraley et al. |
| 2022/0340900 | A1 | 10/2022 | Turunen et al. |
| 2023/0039928 | A1 | 2/2023 | Swildens et al. |
| 2023/0235322 | A1 | 7/2023 | Turunen et al. |
| 2023/0279392 | A1 | 9/2023 | Turunen et al. |
| 2023/0323346 | A1 | 10/2023 | Van Sint Fiet et al. |

FOREIGN PATENT DOCUMENTS

| | | | | |
|---|---|---|---|---|
| EP | 3323890 | A1 | 5/2018 | |
| EP | 3353299 | A1 | 10/2018 | |
| EP | 3353299 | B1 | 3/2020 | |
| EP | 3722420 | A1 | 10/2020 | |
| EP | 4098745 | A1 | 12/2022 | |
| GB | 1610923 | | 8/2016 | |
| JP | 2008194035 | A | 8/2008 | |
| WO | WO-9307883 | A1 | 4/1993 | |
| WO | WO-2000/066604 | A2 | 11/2000 | |
| WO | WO-2004091515 | A2 | 10/2004 | |
| WO | WO-2005007855 | A2 | 1/2005 | |
| WO | WO-2005087949 | A1 | 9/2005 | |
| WO | WO-2005094370 | A2 | 10/2005 | |
| WO | WO-2006042237 | A2 | 4/2006 | |
| WO | WO-2007031091 | A2 | 3/2007 | |
| WO | WO-2007084865 | A2 | 7/2007 | |
| WO | WO-2010/064146 | A2 | 6/2010 | |
| WO | WO-2010115206 | A2 | 10/2010 | |
| WO | WO-2011005761 | A1 | 1/2011 | |
| WO | WO-2011017521 | A2 | 2/2011 | |
| WO | WO-2011072082 | A2 | 6/2011 | |
| WO | WO-2011085271 | A2 | 7/2011 | |
| WO | WO-2011119887 | A1 | 9/2011 | |
| WO | WO-2012006241 | A2 | 1/2012 | |
| WO | WO-2012138487 | A2 | 10/2012 | |
| WO | WO-2013033230 | A1 | 3/2013 | |
| WO | WO-2013075035 | A1 | 5/2013 | |
| WO | WO-2013154798 | A1 | 10/2013 | |
| WO | WO-2014/012081 | A2 | 1/2014 | |
| WO | WO-2014010250 | A1 | 1/2014 | |
| WO | WO-2014011053 | A1 | 1/2014 | |
| WO | WO-2014076196 | A1 | 5/2014 | |
| WO | WO-2014099931 | A1 | 6/2014 | |
| WO | WO-2014179620 | A1 | 11/2014 | |
| WO | WO-2014203518 | A1 | 12/2014 | |
| WO | WO-2014207232 | A1 | 12/2014 | |
| WO | WO-2015107425 | A2 | 7/2015 | |
| WO | WO-2016005514 | A1 | 1/2016 | |
| WO | WO-2016062886 | A1 | 4/2016 | |
| WO | WO-2016/079181 | A1 | 5/2016 | |
| WO | WO-2016/096938 | A1 | 6/2016 | |
| WO | WO-2016/097212 | A1 | 6/2016 | |
| WO | WO-2016089433 | A1 | 6/2016 | |
| WO | WO-2016094845 | A2 | 6/2016 | |
| WO | WO-2016135334 | A1 | 9/2016 | |
| WO | WO-2016138278 | A2 | 9/2016 | |
| WO | WO-2017/015555 | A1 | 1/2017 | |
| WO | WO-2017010556 | A1 | 1/2017 | |
| WO | WO-2017015575 | A1 | 1/2017 | |
| WO | WO-2017050306 | A1 * | 3/2017 | ........... C12N 15/102 |
| WO | WO-2017053431 | A2 | 3/2017 | |
| WO | WO-2017062862 | A2 | 4/2017 | |
| WO | WO-2017100587 | A1 | 6/2017 | |
| WO | WO-2017157899 | A1 | 9/2017 | |
| WO | WO-2017160741 | A1 | 9/2017 | |
| WO | WO-2017/192664 | A1 | 11/2017 | |
| WO | WO-2017186739 | A1 | 11/2017 | |
| WO | WO-2017192679 | A1 | 11/2017 | |
| WO | WO-2017198775 | A1 | 11/2017 | |
| WO | WO-2017/220751 | A1 | 12/2017 | |
| WO | WO-2017210647 | A1 | 12/2017 | |
| WO | WO-2018027078 | A1 | 2/2018 | |
| WO | WO-2018/041973 | A1 | 3/2018 | |
| WO | WO-2018055134 | A1 | 3/2018 | |
| WO | WO-2018067973 | A1 | 4/2018 | |
| WO | WO-2018098264 | A1 | 5/2018 | |
| WO | WO-2018/134301 | A1 | 7/2018 | |
| WO | WO-2018126176 | A1 | 7/2018 | |
| WO | WO-2018223056 | A1 | 12/2018 | |
| WO | WO-2018223073 | A1 | 12/2018 | |
| WO | WO-2018223081 | A1 | 12/2018 | |
| WO | WO-2018237194 | A1 | 12/2018 | |
| WO | WO-2019/005884 | A1 | 1/2019 | |
| WO | WO-2019004939 | A1 | 1/2019 | |
| WO | WO-2019032607 | A1 | 2/2019 | |
| WO | WO-2019043027 | A1 | 3/2019 | |
| WO | WO-2019055951 | A1 | 3/2019 | |
| WO | WO-2019071274 | A1 | 4/2019 | |
| WO | WO-2019075357 | A1 | 4/2019 | |
| WO | WO-2019079347 | A1 | 4/2019 | |
| WO | WO-2019104094 | A2 | 5/2019 | |
| WO | WO-2019111957 | A1 | 6/2019 | |
| WO | WO-2019158475 | A1 | 8/2019 | |
| WO | WO-2019191232 | A2 | 10/2019 | |
| WO | WO-2019200185 | A1 | 10/2019 | |
| WO | WO-2019217784 | A1 | 11/2019 | |
| WO | WO-2019219581 | A1 | 11/2019 | |
| WO | WO-2020001793 | A1 | 1/2020 | |
| WO | WO-2020118246 | A1 | 6/2020 | |
| WO | WO-2020126626 | A1 | 6/2020 | |
| WO | WO-2020154342 | A1 | 7/2020 | |
| WO | WO-2020154343 | A1 | 7/2020 | |
| WO | WO-2020154344 | A1 | 7/2020 | |
| WO | WO-2020157008 | A1 | 8/2020 | |
| WO | WO-2020160336 | A1 | 8/2020 | |
| WO | WO-2020165077 | A1 | 8/2020 | |
| WO | WO-2020191252 | A1 | 9/2020 | |
| WO | WO-2020196662 | A1 | 10/2020 | |
| WO | WO-2020201406 | A1 | 10/2020 | |
| WO | WO-2020211780 | A1 | 10/2020 | |
| WO | WO-2020216637 | A1 | 10/2020 | |
| WO | WO-2020219981 | A2 | 10/2020 | |
| WO | WO-2020219983 | A1 | 10/2020 | |
| WO | WO-2020227691 | A2 | 11/2020 | |
| WO | WO-2020246560 | A1 | 12/2020 | |
| WO | WO-2020252376 | A1 | 12/2020 | |
| WO | WO-2021008447 | A1 | 1/2021 | |
| WO | WO-2021020550 | A1 | 2/2021 | |
| WO | WO-2021060527 | A1 | 4/2021 | |
| WO | WO-2021071788 | A2 | 4/2021 | |

(56) References Cited

FOREIGN PATENT DOCUMENTS

| | | |
|---|---|---|
| WO | WO-2021071858 A1 | 4/2021 |
| WO | WO-2021113270 A1 | 6/2021 |
| WO | WO-2021113390 A1 | 6/2021 |
| WO | WO-2021117729 A1 | 6/2021 |
| WO | WO-2021122998 A1 | 6/2021 |
| WO | WO-2021130313 A1 | 7/2021 |
| WO | WO-2021136404 A1 | 7/2021 |
| WO | WO-2021136408 A1 | 7/2021 |
| WO | WO-2021158921 A2 | 8/2021 |
| WO | WO-2021178237 A2 | 9/2021 |
| WO | WO-2021182474 A1 | 9/2021 |
| WO | WO-2021209010 A1 | 10/2021 |
| WO | WO-2021216853 A1 | 10/2021 |
| WO | WO-2021231673 A1 | 11/2021 |
| WO | WO-2021231675 A1 | 11/2021 |
| WO | WO-2021231679 A1 | 11/2021 |
| WO | WO-2021231680 A1 | 11/2021 |
| WO | WO-2021231685 A1 | 11/2021 |
| WO | WO-2021231691 A1 | 11/2021 |
| WO | WO-2021231692 A1 | 11/2021 |
| WO | WO-2021231698 A1 | 11/2021 |
| WO | WO-2021231830 A1 | 11/2021 |
| WO | WO-2021234459 A1 | 11/2021 |
| WO | WO-2021237223 A1 | 11/2021 |
| WO | WO-2021242778 A1 | 12/2021 |
| WO | WO-2021242870 A1 | 12/2021 |
| WO | WO-2021242889 A1 | 12/2021 |
| WO | WO-2021242903 A2 | 12/2021 |
| WO | WO-2021243023 A1 | 12/2021 |
| WO | WO-2022007803 A1 | 1/2022 |
| WO | WO-2022018207 A1 | 1/2022 |
| WO | WO-2022026928 A1 | 2/2022 |
| WO | WO-2022046667 A1 | 3/2022 |
| WO | WO-2022078569 A1 | 4/2022 |
| WO | WO-2022078995 A1 | 4/2022 |
| WO | WO-2022087272 A1 | 4/2022 |
| WO | WO-2022091100 A1 | 5/2022 |
| WO | WO-2022099159 A1 | 5/2022 |
| WO | WO-2022103839 A1 | 5/2022 |
| WO | WO-2022103852 A1 | 5/2022 |
| WO | WO-2022119975 A2 | 6/2022 |
| WO | WO-2022124345 A1 | 6/2022 |
| WO | WO-2022138929 A1 | 6/2022 |
| WO | WO-2022140264 A1 | 6/2022 |
| WO | WO-2022147573 A1 | 7/2022 |
| WO | WO-2022150974 A1 | 7/2022 |
| WO | WO-2022119975 A3 | 10/2022 |
| WO | WO-2022253810 A1 | 12/2022 |
| WO | WO-2022256283 A2 | 12/2022 |

OTHER PUBLICATIONS

Dawson, et al. (2004) J. Biol. Chem., 279(6): 4941-4951.
International Search Report for PCT/EP2019/062163, mailed Jul. 31, 2019 (6 pages).
Schneider et al. (2014) "Optimal GuideRNAs for Re-directing Deaminase Activity of hADAR1 and hADAR2 in Trans," Nucleic Acids Res., 42(10):e87.
Stafforst et al. (2012) "An RNA-deaminase Conjugate Selectively Repairs Point Mutations," Angewandte Chemie Int. Ed., 51(44): 11166-11169.
UKIPO Search Report for GB1808146.3, mailed Jan. 30, 2019 (5 pages).
Written Opinion for PCT/EP2019/062163, mailed Jul. 31, 2019 (6 pages).
Agrawal, S., et al., "Mixed-Backbone Oligonucleotides Containing Phosphorothioate and Methylphosphonate Linkages as Second Generation Antisense Oligonucleotide," Nucleosides & Nucleotides 16(7-9):927-936, Taylor & Francis, United Kingdom (Aug. 2006).
Agrawal, S., et al., "Mixed-backbone oligonucleotides as second generation antisense oligonucleotides: in vitro and in vivo studies," Proc Natl Acad Sci USA 94(6):2620-2625, National Academy of Sciences, United States (Mar. 1997).
Allain, F.H., et al., "Structural basis of the RNA-binding specificity of human U1A protein," EMBO J 16(18):5764-5772, Wiley-Blackwell, Germany (Sep. 1997).
Lamond, A.I., and Sproat, B.S., "Antisense oligonucleotides made of 2'-O-alkyIRNA: their properties and applications in RNA biochemistry," FEBS Letters 325(1,2):123-127, Wiley-Blackwell, United States (Apr. 1993).
Anonymous, "Phosphonoacetate (PACE) Oligonucleotides," The Glenn Report 20(2):1-4, Glen Research (Oct. 2008).
Aruscavage, P.J., and Bass, B.L., "A phylogenetic analysis reveals an unusual sequence conservation within introns involved in RNA editing," RNA 6(2):257-269, RNA Society, United States (Feb. 2000).
Bajad, P., et al., "A to I editing in disease is not fake news," RNA Biol 14(9): 1223-1231, Taylor & Francis, United Kingdom (Sep. 2017).
Boots, E.A., et al., "BDNF Val66Met predicts cognitive decline in the Wisconsin Registry for Alzheimer's Prevention," Neurology 88(22):2098-2106, Lippincott Williams and Wilkins Ltd., United States (May 2017).
Brown, D.A., et al., "Effect of phosphorothioate modification of oligodeoxynucleotides on specific protein binding," J Biol Chem 269(43):26801-26805, Elsevier, Netherlands (Oct. 1994).
Burchenal, J.H., et al., "Antileukemic effects of pseudoisocytidine, a new synthetic pyrimidine C-nucleoside," Cancer Res 36(4): 1520-1523, American Association for Cancer Research Inc., United States (Apr. 1976).
Burkard, M.E., and Turner, D.H., "Nmr structures of r(GCAGGCGUGC)2 and determinants of stability for single guanosine-guanosine base pairs," Biochemistry 39(38):11748-11762, American Chemical Society, United States (Sep. 2000).
Case, D.A., et al., "The Amber biomolecular simulation programs," J Comput Chem 26(16):1668-1688, John Wiley & Sons Inc. United States (Dec. 2005).
Chen, G., et al., "RNA-Guided Adenosine Deaminases: Advances and Challenges for Therapeutic RNA Editing," Biochemistry 58(15):1947-1957, American Chemical Society, United States (Apr. 2019).
Dawson, T.R., et al., "Structure and sequence determinants required for the RNA editing of ADAR2 substrates," J Biol Chem 279(6):4941-4951, Elsevier, Netherlands (Feb. 2004).
Deleavey, G.F., and Damha, M.J., "Designing chemically modified oligonucleotides for targeted gene silencing," Chem Biol 19(8):937-954, American Chemical Society, United States (Aug. 2012).
Desterro, J.M.P., et al., "Dynamic association of RNA-editing enzymes with the nucleolus," J Cell Sci 116(Pt 9):1805-1818, Company of Biologists Ltd, United Kingdom (May 2003).
Diaz, A., et al., "Unusual Cys-Tyr covalent bond in a large catalase," J Mol Biol 342(3):971-985, Elsevier, Netherlands (Sep. 2004).
Doherty, E., et al., "Rational Design of RNA Editing Guide Strands: Cytidine Analogs at the Orphan Position," J Am Chem Soc 143(18):6865-6876, American Chemical Society, United States (May 2021).
Eggington, J. M., et al., "Predicting Sites of ADAR Editing in Double-stranded RNA," Nature Communications 2(1):319, pp. 1-9, Nature Publishing Group, United Kingdom (May 2011).
Flur, S. and Micura, R., "Chemical Synthesis of RNA With Site-specific Methylphosphonate Modifications," Methods 107:79-88, Academic Press, United States (Sep. 2016).
Fukuda, M., et al., "Construction of a guide-RNA for site-directed RNA mutagenesis utilising intracellular A-to-I RNA editing," Sci Rep 7:41478, Nature Publishing Group, United Kingdom (Feb. 2017).
Garncarz, W., et al., "A High-throughput Screen to Identify Enhancers of ADAR-mediated RNA-editing," RNA Biology 10(2): 192-204, Landes Bioscience, United States (Feb. 2013).
Girard, A., et al., "A germline-specific class of small RNAs binds mammalian Piwi proteins," Nature 442(7099): 199-202, Nature Publishing Group, United Kingdom (Jul. 2006).
Grünewald, A., et al., "Does uncoupling protein 2 expression qualify as marker of disease status in LRRK2-associated Parkinson's disease?" Antioxid Redox Signal 20(13):1955-1960, Mary Ann Liebert, Inc., United States (May 2014).

(56) References Cited

OTHER PUBLICATIONS

Hallegger, M., et al., "RNA Aptamers Binding the Double-stranded RNA-binding Domain," RNA 12(11):1993-2004, Cold Spring Harbor Laboratory Press, United States (Nov. 2006).

Hamma, T., and Miller, P.S., "Syntheses of Alternating Oligo-2'-O-methylribonucleoside Methylphosphonates and their Interactions with HIV TAR RNA," Biochemistry 38(46):15333-15342, American Chemical Society, United States (Nov. 1999).

Harrow, J., et al., "GENCODE: the reference human genome annotation for The ENCODE Project," Genome Res 22(9):1760-1774, Cold Spring Harbor Laboratory Press, United States (Sep. 2012).

Haudenschild, B. L., et al., "A Transition State Analogue for an RNA-editing Reaction," Journal of the American Chemical Society 126(36):11213-11219, American Chemical Society, United States (Sep. 2004).

Herrmann, T., et al., "Protein NMR structure determination with automated NOE assignment using the new software CANDID and the torsion angle dynamics algorithm DYANA," J Mol Biol 319(1):209-27, Elsevier, Netherlands (May 2002).

Higuchi, M., et al., "RNA Editing of AMPA Receptor Subunit GluR-B: a Base-paired Intron-exon Structure Determines Position and Efficiency," Cell 75:1361-1370, Cell Press, United States (Dec. 1993).

Ikehara, M., et al., "Nucleosides and Nucleotides. Xl Vii. Conformation of Purine Nucleosides and their 5'-phosphates" Biochemistry 11(5):830-836, American Chemical Society, United States (Feb. 1972).

Iwamoto, N., et al., "Control of phosphorothioate stereochemistry substantially increases the efficacy of antisense oligonucleotides," Nat Biotechnol 35(9):845-851, Nature Publishing Group, United Kingdom (Sep. 2017).

Jiang, F., et al., "Structural Basis of RNA Folding and Recognition in an AMP-RNA Aptamer Complex," Nature 382: 183-186, Nature Publishing Group, United Kingdom (Jul. 1996).

Juliano, R.L., et al., "Cellular Uptake and Intracellular Trafficking of Antisense and siRNA Oligonucleotides," Bioconjugate Chemistry 23(2):147-157, American Chemical Society, United States (Feb. 2012).

Juliano, R.L., "The Delivery of Therapeutic Oligonucleotides," Nucleic Acids Research 44(14):6518-6548, Oxford University Press, United Kingdom (Aug. 2016).

Katrekar, D., et al., "In vivo RNA editing of point mutations via RNA-guided adenosine deaminases," Nature Methods 16(3):239-242, Nature Publishing Group, United Kingdom (Mar. 2019).

Kean, J.M., et al., "Inhibition of Herpes Simplex Virus Replication by Antisense Oligo-2'-0-methylribonucleoside Methylphosphonates," Biochemistry 34(45): 14617-14620, American Chemical Society, United States (Nov. 1995).

Kumar, M. and Carmichael, G.G., "Antisense RNA: Function and Fate of Duplex RNA in Cells of Higher Eukaryotes," Microbiology and Molecular Biology Reviews 62(4):1415-1434, American Society for Microbiology, United States (Dec. 1998).

Kuttan, A., and Bass, B.L., "Mechanistic Insights Into Editing-site Specificity of ADARs," Proc Natl Acad Sci USA 109(48):E3295-E3304, National Academy of Sciences, United States (Nov. 2012).

Penn, A.C., et al., "Steric Antisense Inhibition of AMPA Receptor Q/R Editing Reveals Tight Coupling to Intronic Editing Sites and Splicing," Nucleic Acids Research 41(2):1113-1123, Oxford Academic Press, United Kingdom (Jan. 2013).

Lancaster, M., and Knoblich, J., "Organogenesis in a dish: modeling development and disease using organoid technologies," Science 345(6194): 1247125, American Association for the Advancement of Science, United States (Jul. 2014).

Lennox, K.A., and Behlke, M.A., "Chemical Modification and Design of Anti-miRNA Oligonucleotides," Gene Therapy 18(12):1111-1120, Nature Publishing Group, United Kingdom (Dec. 2011).

Lomeli, H., et al., "Control of kinetic properties of AMPA receptor channels by nuclear RNA editing," Science 266(5191):1709-1713, American Association for the Advancement of Science, United States (Dec. 1994).

Lu, J., et al., "Synthesis of Pyridine, Pyrimidine and Pyridinone C-nucleoside Phosphorarnidites for Probing Cytosine Function in RNA," The Journal of Organic Chemistry 74:8021-8030, American Chemical Society, United States (Nov. 2009).

Macbeth, M. R., et al., "Evidence for Auto-inhibition by the N Terminus of hADAR2 and Activation by dsRNA Binding," RNA 10:1563-1571, Cold Spring Harbor Laboratory Press, United States (Oct. 2004).

Macbeth, M. R., and Bass, B. L., "Large-scale Overexpression and Purification of ADARs from *Saccharomyces* Cerevisiae for Biophysical and Biochemical Studies," Methods in Enzymology 424:319-331, Elsevier, Netherlands (Jan. 2007).

Malik, T., et al., "Regulation of RNA editing by intracellular acidification," Nucleic Acids Res 49(7):4020-4036, Oxford University Press, United Kingdom (Apr. 2021).

Matsui, M., et al., "Effect of 2'-O-methyl/thiophosphonoacetate-modified Antisense Oligonucleotides on Huntingtin Expression in Patient-derived Cells," Artificial DNA: PNA & XNA 5(3):e1146391, Taylor & Francis, United Kingdom (Dec. 2014).

Masliah, G., et al., "RNA Recognition by Double-stranded RNA Binding Domains: a Matter of Shape and Sequence," Cellular and Molecular Life Sciences 70(11):1875-1895, Springer, Switzerland (Jun. 2013).

Matthews, M., et al., "Structures of human ADAR2 bound to dsRNA reveal base-flipping mechanism and basis for site selectivity," Nat Struct Mol Biol 23(5):426-33, Nature Publishing Group, United Kingdom (May 2016).

Mei, D., et al., "Therapeutic RNA Strategies for Chronic Obstructive Pulmonary Disease," Trends Pharmacol Sci 41(7):475-486, Elsevier, Netherlands (Jul. 2020).

Merkle, T., et al., "Precise RNA editing by recruiting endogenous ADARs with antisense oligonucleotides," Nature Biotechnology 37(2):133-138, Nature Publishing Group, United Kingdom (Feb. 2019).

Mizrahi, R.A., et al., "Potent and Selective Inhibition of A-to-I RNA Editing With 2'-O-methyl/locked Nucleic Acid-containing Antisense Oligoribonucleotides," ACS Chemical Biology 8(4):832-839, American Chemical Society, United States (Apr. 2013).

Veliz, E.A., et al., "Substrate Analogues for an RNA-editing Adenosine Deaminase: Mechanistic Investigation and Inhibitor Design," Journal of the American Chemical Society 125(36):10867-10876, American Chemical Society, United States (Sep. 2003).

Montiel-Gonzalez M.F., et al., "An efficient system for selectively altering genetic information within mRNAs," Nucleic Acids Res. 44(21):e157, Oxford Academic Press, United Kingdom (Dec. 2016).

Montiel-Gonzalez, M.F., et al., "Current strategies for Site-Directed RNA Editing using ADARs," Methods 156:16-24, Elsevier, Netherlands (Mar. 2019).

Murayama, K., et al., "Highly Stable Duplex Formation by Artificial Nucleic Acids Acyclic Threoninol Nucleic Acid (aTNA) and Serinol Nucleic Acid (SNA) with Acyclic Scaffolds," Chemistry-A European Journal 19:14151-14158, Wiley-VCH Verlag, Germany (Oct. 2013).

Nelwan, M., "Treat Oculocutaneous Albinism with Gene Therapy," Journal of Advances in Biology & Biotechnology 16(3):1-12, Hooghly: ScienceDomain International, India (Jan. 2018).

Nishikura, K., "Functions and Regulation of RNA Editing by ADAR Deaminases," Annual Review of Biochemistry 79:321-349, Annual Reviews, United States (Oct. 2010).

Nose, K. et al., "Short-Chain Guide RNA for Site-Directed A-to-I RNA Editing," Nucleic Acid Ther 31(1):58-67, Mary Ann Liebert, United States (Feb. 2021).

Nottrott, S., et al., "Functional interaction of a novel 15.5kD [U4/U6.U5] tri-snRNP protein with the 5' stem-loop of U4 snRNA," EMBO J 18(21):6119-33, EMBO, Germany (Nov. 1999).

Pan, B., et al., "Crystal Structure of an RNA 16-mer Duplex R(GCAGAGUUAAAUCUGC)2 With Nonadjacent G(Syn) A+(Anti) Mispairs," Biochemistry 38(9):2826-2831, American Chemical Society, United States (Mar. 1999).

(56) References Cited

OTHER PUBLICATIONS

Papkovskaia, T.D., et al., "G2019S Leucine-rich Repeat Kinase 2 Causes Uncoupling Protein-mediated Mitochondrial Depolarization," Human Molecular Genetics 21(19):4201-4213, IRL Press at Oxford University Press, United Kingdom (Oct. 2012).
Pasternak, A., and Wengel, J., "Unlocked Nucleic Acid—an RNA Modification With Broad Potential," Organic & Biomolecular Chemistry 9:3591-3597, Royal Society of Chemistry, United Kingdom (Mar. 2011).
Qu, L., et al., "Programmable RNA editing by recruiting endogenous ADAR using engineered RNAs," Nature Biotechnology 37(9): 1059-1069, Nature Publishing Group, United Kingdom (Sep. 2019).
Rieder, L. E., et al., "Tertiary Structural Elements Determine the Extent and Specificity of Messenger RNA Editing," Nature Communications 4:2232, Nature Publishing Group, United Kingdom (Aug. 2013).
Vogel, P., and Stafforst, T., "Critical review on engineering deaminases for site-directed RNA editing," Current Opinion in Biotechnology 55:74-80, Elsevier, Netherlands (Feb. 2019).
Ryan, D., et al., "Improving CRISPR-Cas specificity with chemical modifications in single-guide RNAs," Nucleic Acids Res 46(2):792-803, Oxford Academic Press, United Kingdom (Jan. 2018).
Saccomanno, L. and Bass, B.L., "A Minor Fraction of Basic Fibroblast Growth Factor mRNA is Deaminated in *Xenopus* Stage VI and Matured Oocytes," RNA 5(1):39-48, Cold Spring Harbor Laboratory Press, United States (Jan. 1999).
Sala, F.G., et al., "Tissue-engineered Small Intestine and Stomach Form From Autologous Tissue in a Preclinical Large Animal Model," The Journal of Surgical Research 156(2):205-212, Academic Press, United States (Oct. 2009).
Sato, T., et al., "Long-term Expansion of Epithelial Organoids From Human Colon, Adenoma, Adenocarcinoma, and Barrett's Epithelium," Gastroenterology 141(5):1762-1772, W.B. Saunders, United States (Nov. 2011).
Schade, M., et al., "A 6 bp Z-DNA Hairpin Binds Two Z Alpha Domains From the Human RNA Editing Enzyme ADAR1," Febs Letters 458(1):27-31, John Wiley & Sons Ltd., United Kingdom (Sep. 1999).
Schneider, M.F., et al., "Optimal guideRNAs for re-directing deaminase activity of hADAR1 and hADAR2 in trans," Nucleic Acids Res 42(10):e87, Oxford University Press, United Kingdom (Jun. 2014).
Schweitzer, M., and Engels, J.W., "Sequence Specific Hybridization Properties of Methylphosphonate Oligodeoxynucleotides," Journal of Biomolecular Structure and Dynamics 16(6):1177-1188, Taylor & Francis, United Kingdom (Jun. 1999).
Sharma, V.K. and Watts, J.K., "Oligonucleotide Therapeutics: Chemistry, Delivery and Clinical Progress," Future Medicinal Chemistry 7(16):2221-2242, Future Science, United Kingdom (Oct. 2015).
Sheehan, D., et al., "Biochemical Properties of Phosphonoacetate and Thiophosphonoacetate Oligodeoxyribonucleotides," Nucleic Acids Research 31(14):4109-4118, Oxford Academic Press, United Kingdom (Jul. 2003).
Singleton, M., et al., "X-ray structure of pyrrolidone carboxyl peptidase from the hyperthermophilic archaeon *Thermococcus litoralis*," Structure 7(3):237-244, Cell Press, United Kingdom (Mar. 1999).
Sipova, H., et al., "5'-O-Methylphosphonate Nucleic Acids—new Modified DNAs that Increase the *Escherichia coli* RNase H Cleavage Rate of Hybrid Duplexes," Nucleic Acids Research 42(8):5378-5389, Oxford Academic Press, United Kingdom (Apr. 2014).
Smith, G.A., et al., "Fibroblast Biomarkers of Sporadic Parkinson's Disease and LRRK2 Kinase Inhibition," Molecular Neurobiology 53(8):5161-5177, Humana Press, United States (Oct. 2016).
Stafforst, T., and Schneider, M.F., "An RNA-deaminase conjugate selectively repairs point mutations," Angew Chem Int Ed Engl 51(44): 11166-11169, Wiley-VCH, Germany (Oct. 2012).
Stefl, R., and Allain, F. H., "A Novel RNA Pentaloop Fold Involved in Targeting ADAR2," RNA 11(5):592-597, Cold Spring Harbor Laboratory, United States (May 2005).
Stefl, R., et al., "Structure and specific RNA binding of ADAR2 double-stranded RNA binding motifs," Structure 14(2):345-355, Cell Press, United Kingdom (Feb. 2006).
Svoboda, P., and Di Cara, A., "Hairpin RNA: a Secondary Structure of Primary Importance," Cellular and Molecular Life Sciences 63(7):901-908, Birkhauser Verlag, Switzerland (Apr. 2006).
Thuy-Boun, A.S., et al., "Asymmetric dimerization of adenosine deaminase acting on RNA facilitates substrate recognition," Nucleic Acids Res 48(14):7958-7972, Oxford University Press, United Kingdom (Aug. 2020).
Tian, B., et al., "The double-stranded-RNA-binding motif: interference and much more," Nat Rev Mol Cell Biol 5(12):1013-1023, Nature Publishing Group, United Kingdom (Dec. 2004).
Tian, N., et al., "A structural determinant required for RNA editing," Nucleic Acids Res 39(13):5669-5681, Oxford University Press, United Kingdom (Jul. 2011).
ProQR Therapeutics, "Axiomer® technology: Therapeutic oligonucleotides for directing site-specific A-to-I editing by endogenous ADAR enzymes," Presentation, accessed at www.proqr.com, 21 pages (Sep. 2021).
Vaish, N., et al., "Improved Specificity of Gene Silencing by siRNAs Containing Unlocked Nucleobase Analogs," Nucleic Acids Research 39(5):1823-1832, Oxford Academic Press, United Kingdom (Mar. 2011).
Vogel, P., et al., "Improving site-directed RNA editing in vitro and in cell culture by chemical modification of the guideRNA," Angew Chem Int Ed Engl 53(24):6267-6271, Wiley-VCH, Germany (Jun. 2014).
Vogel, P. and Stafforst, T., "Site-directed RNA Editing With Antagomir Deaminases—a Tool to Study Protein and RNA Function," ChemMedChem 9(9):2021-2025, Wiley-VCH, Germany (Sep. 2014).
Wang, M., et al., "Saponins enhance exon skipping of 2'-O-methyl phosphorothioate oligonucleotide in vitro and in vivo," Drug Des Devel Ther 12:3705-3715, Dove Press, United Kingdom (Oct. 2018).
Wong, S. K., et al., "Substrate Recognition by ADAR1 and ADAR2," RNA 7:846-858, Cold Spring Harbor Laboratory, United States (Jun. 2001).
Yang, Z., et al., "Artificially expanded genetic information system: a new base pair with an alternative hydrogen bonding pattern," Nucleic Acids Res 34(21):6095-6101, Oxford University Press, United Kingdom (Dec. 2006).
Zangemeister-Wittke, U., et al., "A Novel Bispecific Antisense Oligonucleotide Inhibiting both bcl-2 and bcl-xL Expression Efficiently Induces Apoptosis in Tumor Cells," Clinical Cancer Research 6(6):2547-2555, The Association of Clinical Cancer Research, United States (Jun. 2000).
Zheng, Y., et al., "DNA editing in DNA/RNA hybrids by adenosine deaminases that act on RNA," Nucleic Acids Research 45(6):3369-3377, Oxford University Press, United Kingdom (Apr. 2017).
Zhou, P., et al., "Geometric characteristics of hydrogen bonds involving sulfur atoms in proteins," Proteins 76(1):151-63, John Wiley & Sons Inc. United States (Jul. 2009).
Fry, L., et al., "RNA Editing as a Therapeutic Approach for Retinal Gene Therapy Requiring Long Coding Sequences," International Journal Molecular Sciences, 21(3): 777, MDPI, Switzerland (Jan. 2020).
Maydanovych, O., et al., "Probing Adenosine-to-inosine Editing Reactions Using RNA-containing Nucleoside Analogs," Methods in Enzymology 424:369-386, Elsevier, Netherlands (Jan. 2007).
Di Giorgio, S., et al., "Evidence for host-dependent RNA editing in the transcriptome of SARS-CoV-2," Sci Adv 6(25): eabb5813, American Association for the Advancement of Science, United States (Jun. 2020).
Kung, C., et al., "The Role of RNA Editing in Cancer Development and Metabolic Disorders," Frontiers in Endocrinology, 9:762, Frontiers Media, Switzerland (Dec. 2018).
Schirle, N., et al., "Selective inhibition of ADAR2-catalyzed editing of the serotonin 2c receptor pre-mRNA by a helix-threading peptide," Organic and Biomolecular Chemistry, 8(21):4898-904, Royal Society of Chemistry, United Kingdom (Nov. 2010).

(56) References Cited

OTHER PUBLICATIONS

Xu, L.-D., and Öhman, M., "ADAR1 Editing and its Role in Cancer," Genes (Basel) 10(1):12 pages, MDPI, Switzerland (Dec. 2018).
Declaration of Strawman Limited in Notice of Opposition mailed Feb. 25, 2021 in EP Application No. 15813826.3, European Patent Office, United Kingdom, 33 pages.
Declaration of Margaret Dixon Limited in Notice of Opposition mailed Feb. 25, 2021 in EP Application No. 15813826.3, European Patent Office, Germany, 44 pages.
Declaration of Margaret Dixon Limited in Notice of Opposition mailed Jun. 25, 2021 in EP Application No. 17771348.4, European Patent Office, Germany, 35 pages.
Written Opinion for International Application No. PCT/EP2015/080347, European Patent Office, Netherlands, mailed on Apr. 1, 2016, 5 pages.
Written Opinion for International Application No. PCT/EP2017/065467, European Patent Office, Netherlands, mailed on Sep. 15, 2017, 5 pages.
Written Opinion for International Application No. PCT/EP2017/071912, European Patent Office, Netherlands, mailed on Mar. 26, 2019, 5 pages.
Written Opinion for International Application No. PCT/EP2018/051202, European Patent Office, Netherlands, mailed on Mar. 19, 2018, 7 pages.
Written Opinion for International Application No. PCT/EP2019/053291, European Patent Office, Netherlands, mailed on Jun. 6, 2019, 5 pages.
Written Opinion for International Application No. PCT/EP2019/062163, European Patent Office, Netherlands, mailed on Jul. 31, 2019, 6 pages.
International Preliminary Report on Patentability for International Application No. PCT/EP2020/051931, The International Bureau of WIPO, mailed on Jul. 27, 2021, 7 pages.
Written Opinion for International Application No. PCT/EP2020/053283, European Patent Office, Netherlands, mailed on Jul. 17, 2020, 11 pages.
International Preliminary Report on Patentability for International Application No. PCT/EP2020/059369, The International Bureau of WIPO, mailed on Sep. 28, 2021, 6 pages.
International Preliminary Report on Patentability for International Application No. PCT/EP2020/060291, The International Bureau of WIPO, mailed on Sep. 28, 2021, 6 pages.
Written Opinion for International Application No. PCT/US2020/037580, European Patent Office, Netherlands, mailed on Oct. 2, 2020, 7 pages.
Written Opinion for International Application No. PCT/EP2020/087767, European Patent Office, Netherlands, mailed on Apr. 16, 2021, 7 pages.
Written Opinion for International Application No. PCT/EP2021/070535, European Patent Office, Netherlands, mailed on Nov. 3, 2021, 6 pages.
Christofi, T., and Zaravinos, A., "Rna editing in the forefront of epitranscriptomics and human health," Journal of Translational Medicine, 17(1):319, BioMed Central, United Kingdom (Sep. 2019).
Jain, M., et al., "The Editor's I on Disease Development," Trends in Genetics, 35(12):903-913, Elsevier, Netherlands (Dec. 2019).
Monteleone, L. R., et al., "A Bump-Hole Approach for Directed RNA Editing," Cell Chemical Biology 26(2):269-277, Cell Press, United States (Feb. 2019).
Rovai, A., et al., "In vivo adenine base editing reverts C282Y and improves iron metabolism in hemochromatosis mice," Nature Communications, 13(1):5215, Nature Publishing Group, United Kingdom (Sep. 2022).
Savva, Y., et al., "The ADAR protein family," Genome Biology, 13(12):252 BioMed Central, United Kingdom (Dec. 2012).
Ahmadzadeh, M., et al., "Tumor Antigen-specific CD8 T Cells Infiltrating the Tumor Express High Levels of PD-1 and Are Functionally Impaired, " Blood 114(8): 1537-1544, American Society of Hematology, United States (Aug. 2009).

Baitsch, L., et al., "Exhaustion of Tumor-specific CD8+ T Cells in Metastases From Melanoma Patients," The Journal of Clinical Investigation 121(6):2350-2360, American Society for Clinical Investigation, United States (Jun. 2011).
Barber, D.L., et al., "Restoring Function in Exhausted CD8 T Cells during Chronic Viral Infection," Nature 439(7077):682-687, Nature Publishing Group, United States (Feb. 2006).
Blackburn, S.D., et al., "Coregulation of CD8+ T cell exhaustion by multiple inhibitory receptors during chronic viral infection," Nature Immunology 10(1):29-37, Nature Publishing Group, United Kingdom (Jan. 2009).
Boni, C., et al., "Characterization of Hepatitis B Virus (HBV)-Specific T-Cell Dysfunction in Chronic HBV Infection," Journal of Virology 81(8):4215-4225, American Society For Microbiology, United States (Apr. 2007).
Brown, D.A., et al., "Effect of Phosphorothioate Modification of Oligodeoxynucleotides on Specific Protein Binding," The Journal of Biological Chemistry 269(43):26801-26805, Elsevier Inc., United States (Oct. 1994).
Carreno, B.M., et al., "The B7 Family of Ligands and its Receptors: New Pathways for Costimulation and Inhibition of Immune Responses," Annual Review of Immunology 20:29-53, Annual Reviews Inc., United States (Apr. 2002).
Case, D.A., et al., "The Amber Biomolecular Simulation Programs," Journal of Computational Chemistry 26(16):1668-1688, Wiley, United States (Dec. 2005).
Channappanavar, R., et al., "T Cell-mediated Immune Response to Respiratory Coronaviruses," Immunologic Research 59(1-3):118-128, Humana Press, United States (Aug. 2014).
Curran, M.A., et al., "PD-1 and CTLA-4 Combination Blockade Expands Infiltrating T Cells and Reduces Regulatory T and Myeloid Cells within B16 Melanoma Tumors," Proceedings of the National Academy of Sciences, USA 107(9):4275-4280, National Academy of Sciences, United States (Mar. 2010).
Dawson, T.R., et al., "Structure and Sequence Determinants Required for the RNA Editing of ADAR2 Substrates," The Journal of Biological Chemistry 279(6):4941-4951, Elsevier Inc., United States (Feb. 2004).
Day, C.L., et al., "PD-1 expression on HIV-specific T cells is associated with T-cell exhaustion and disease progression," Nature 443(7109):350-354, Nature Publishing Group, United Kingdom (Sep. 2006).
Diaz, A., et al., "Unusual Cys-Tyr covalent bond in a large catalase," Journal of Molecular Biology 342(3):971-985, Elsevier, Netherlands (Sep. 2004).
Document D10 cited in Opposition of European Patent No. 3234134 "Structure of the CF4 oligonucleotide of WO2005/094370", RNAfold WebServer, retrieved on Feb. 25, 2021, 05 pages.
Document D12 cited in Opposition of European Patent No. 3234134 "Structure of Seq Id No. 1 of WO2014/011053", RNAfold WebServer retrieved on Feb. 25, 2021, 05 pages.
Document D3 cited in Opposition of European Patent No. 3234134, "Structure of the 25mer of Woolf et al., Proceedings of the National Academy of Sciences of the United States of America, 92(18):8298-8302.".
Document D8 cited in Opposition of European Patent No. 3234134 "Examples of pairs of known RNA sequences in which one of the pairs meets the requirements of the Patent", RNAfold WebServer, retrieved on Feb. 24, 2021, 20 pages.
Dolina, J.S., et al., "Lipidoid nanoparticles containing PD-L1 siRNA delivered in vivo enter Kupffer cells and enhance NK and CD8(+) T cell-mediated hepatic antiviral immunity," Molecular Therapy Nucleic Acids 2(2):e72, 1-14, Cell Press, United States (Feb. 2013).
Dracheva, S., et al., "Increased serotonin 2C receptor mRNA editing: a possible risk factor for suicide," Molecular Psychiatry 13(11):1001-1010, Nature Publishing Group, United Kingdom (Nov. 2008).
Egholm, M., et al., "PNA Hybridizes to Complementary Oligonucleotides Obeying the Watson-crick Hydrogen-bonding Rules," Nature 365(6446):566-568, Nature Publishing Group, United Kingdom (Oct. 1993).
Erickson, J.J., et al., "Viral Acute Lower Respiratory Infections Impair CD8+ T Cells Through PD-1," The Journal of Clinical

(56) References Cited

OTHER PUBLICATIONS

Investigation 122(8):2967-2982, American Society for Clinical Investigation, United States (Aug. 2012).
Fukuda, M., et al., "Identification of an RNA element for specific coordination of A-to-I RNA editing on HTR2C pre-mRNA," Genes on Cells 20:834-846, The Molecular Biology Society of Japan & Wiley Publishing Asia (Oct. 2015).
Giorgio, S.D., et al., "Evidence for RNA Editing in the Transcriptome of 2019 Novel Coronavirus," 24 Pages, (Mar. 2020).
Golden-Mason, L., et al., "Upregulation of PD-1 Expression on Circulating and Intrahepatic Hepatitis C Virus-specific CD8+ T Cells Associated With Reversible Immune Dysfunction," Journal of Virology 81(17):9249-9258, American Society For Microbiology, United States (Sep. 2007).
He, X.H., et al., "Identification of a Novel Splice Variant of Human PD-L1 mRNA Encoding an Isoform-lacking Igv-like Domain," Acta Pharmacologica Sinica 26(4):462-468, Nature Publishing Group, United States (Apr. 2005).
Hofler, S., and Carlomagno, T., "Structural and Functional Roles of 2'-o-ribose Methylations and Their Enzymatic Machinery Across Multiple Classes of RNAs," Current Opinion in Structural Biology 65:42-50, Elsevier Ltd., United Kingdom (Dec. 2020).
Huang, Y., "Preclinical and Clinical Advances of GalNAc-Decorated Nucleic Acid Therapeutics," Molecular Therapy. Nucleic Acids 6:116-132, Cell Press, United States (Mar. 2017).
International Search Report and Written Opinion for Application No. PCT/EP2020/059369, European Patent Office, mailed on Jul. 13, 2020, 11 pages.
International Search Report and Written Opinion for International Application No. PCT/EP2020/058828, European Patent Office, Netherlands, dated Jul. 17, 2020, 13 pages.
International Search Report and Written Opinion for International Application No. PCT/EP2020/060291, mailed Jul. 22, 2020, 11 pages.
Iwamoto, N., et al., "Control of Phosphorothioate Stereochemistry Substantially Increases the Efficacy of Antisense Oligonucleotides," Nature Biotechnology 35(9):845-851, Nature America Publishing, United States (Sep. 2017).
Jiang, G.M., et al., "The Relationship Between Autophagy and the Immune System and its Applications for Tumor Immunotherapy," Molecular Cancer 18(1):17, BioMed Central, United Kingdom (Jan. 2019).
Kahan, S.M. and Zajac, A.J., "Immune Exhaustion: Past Lessons and New Insights from Lymphocytic Choriomeningitis Virus," Viruses 11(2):156, MDPI, Switzerland (Feb. 2019).
Kudo, M., "Immune Checkpoint Inhibition in Hepatocellular Carcinoma: Basics and Ongoing Clinical Trials," Oncology 92(Suppl 1):50-62, Karger, Switzerland (Sep. 2017).
Lancaster, M.A. and Knoblich, J.A., "Organogenesis in a Dish: Modeling Development and Disease Using Organoid Technologies," Science 345(6194):1247125, American Association for the Advancement of Science, United States (Jul. 2014).
Lorenz, R., et al., "Vienna RNA Package 2.0," Algorithms for Molecular Biology 6:26, 1-14, BioMed Central, United Kingdom (Nov. 2011).
Maier, H., et al., "PD-1:PD-L1 Interactions Contribute to the Functional Suppression of Virus-specific CD8+ T Lymphocytes in the Liver," Journal of Immunology 178(5):2714-2720, American Association of Immunologists, United States (Mar. 2007).
Masatora, et al., "SCORE Search Results Details for Application 15531164 and Search Result 20190520_1," 2015, 1 page.
Matthews, M.M., et al., "Structures of Human ADAR2 Bound to dsRNA Reveal Base-flipping Mechanism and Basis for Site Selectivity," Nature Structural & Molecular Biology 23(5):426-433, Nature Pub Group, United States (May 2016).
McNally, B., et al., "Local Blockade of Epithelial PDL-1 in the Airways Enhances T Cell Function and Viral Clearance During Influenza Virus Infection," Journal of Virology 87(23):12916-12924, American Society for Microbiology, United States (Dec. 2013).

Mizrahi, et al., "Potent and Selective Inhibition of A-to-I RNA Editing with 2'-O-Methyl/Locked Nucleic Acid-containing Antisense Oligoribonucleotides," ACS Chemical Biology Supporting Information 1-4, American Chemical Society, United States (Apr. 2013).
Montiel-Gonzalez, M. F., et al., "Correction of Mutations Within the Cystic Fibrosis Transmembrane Conductance Regulator by Site-directed RNA Editing," Proc Natl Acad Sci USA 110(45):18285-18290, National Academy of Sciences, United States (Nov. 2013).
Montiel-Gonzalez, M.F., et al., "An Efficient System for Selectively Altering Genetic Information Within mRNAs," Nucleic Acids Research 44(21):e157, 12 Pages, Oxford University Press, United Kingdom (Dec. 2016).
Morita, K., et al., "2'-0,4'-C-ethylene-bridged Nucleic Acids (ENA) with Nuclease-resistance and High Affinity for RNA," Nucleic Acids Research. Supplement (Suppl 1):241-242, Oxford University Press, United Kingdom (Nov. 2001).
Nielsen, P.E., et al., "Sequence-Selective Recognition of DNA by Strand Displacement with a Thymine-Substituted Polyamide," Science 254(5037):1497-1500, American Association for the Advancement of Science, United States (Dec. 1991).
Nose, K., et al., "Short-Chain Guide RNA for Site-directed A-to-I RNA Editing," Nucleic Acid Therapeutics 00(00): 1-95, Mary Ann Liebert, United States (Feb. 2020).
Notice of Opposition by Margaret Dixon Limited, against European Patent No. 3234134, dated Feb. 25, 2021.
Notice of Opposition by Margaret Dixon Limited, against European Patent No. 3507366, dated Jun. 25, 2021.
Odorizzi, P.M., et al., "Genetic Absence of PD-1 Promotes Accumulation of Terminally Differentiated Exhausted CD8+ T Cells," The Journal of Experimental Medicine 212(7):1125-1137, Rockefeller University Press, United States (Jun. 2015).
Rutten, J.W., et al., "Therapeutic NOTCH3 Cysteine Correction in CADASIL Using Exon Skipping: in Vitro Proof of Concept," Brain 139(Pt 4):1123-1135, Oxford University Press, United Kingdom (Apr. 2016).
Salata, C., et al., "Coronaviruses: A Paradigm of New Emerging Zoonotic Diseases," Pathogens and Disease 77(9):ftaa006, Oxford University Press, United Kingdom (Dec. 2019).
Schneider, M.F., et al., "Supporting Information: Optimal GuideRNAs for Re-directing Deaminase Activity of hADAR1 and hADAR2 in Trans," URL: (http://nar.oxfordjournals.org/content/suppl/2014/04/05/gku272.DC1/nar-03496-met-g-2013-File007.pdf), 15 pages (Jun. 2014).
Score Result to Fukuoka University (2015).
Score Result to LEVANON, et al., WO2005-087949 (2005).
Search Report for GB1700939.0, dated Oct. 1, 2017 (2 pages).
Sharpe, A.H. and Pauken, K.E., "The Diverse Functions of the PD1 Inhibitory Pathway," Nature Reviews. Immunology 18(3):153-167, Nature Publishing Group, United Kingdom (Mar. 2018).
Shevchenko, G. and Morris, K.V., "All I's on the RADAR: Role of ADAR in Gene Regulation," FEBS Letters 592(17):2860-2873, John Wiley & Sons Ltd., United Kingdom (Sep. 2018).
Singleton, M., et al., "X-ray Structure of Pyrrolidone Carboxyl Peptidase From the Hyperthermophilic Archaeon *Thermococcus litoralis*," Structure 7(3):237-244, Cell Press, United States (Mar. 1999).
Stafforst, T. and Schneider, M.F., "Supporting Information: An RNA-deaminase Conjugate Selectively Repairs Point Mutations, " URL: PQR-013_https://onlinelibrary.wiley.com/action/downloadSupplement?doi=10.1002%2Fanie.201206489&file=anie_201206489_sm_miscellaneous_information.pdf (23 pages) (Oct. 2012).
Statement of Opposition by Strawman Limited, against European Patent No. 3234134, of PROQR Therapeutics II B.V., dated Feb. 25, 2021.
Stefl, R., et al., "Structure and Specific RNA Binding of ADAR2 Double-stranded RNA Binding Motifs," Structure 14(2):345-355, Cell Press, United States (Feb. 2006).
Østergaard, M.E., et al., "Efficient Synthesis and Biological Evaluation of 5'-GalNAc Conjugated Antisense Oligonucleotides," Bioconjugate Chemistry 26(8):1451-1455, American Chemical Society, United States (Aug. 2015).

(56) References Cited

OTHER PUBLICATIONS

Sznol, M., "Blockade of the B7-H1/PD-1 Pathway as a Basis for Combination Anticancer Therapy," Cancer Journal 20(4):290-295, Lippincott Williams & Wilkins, United States (Jul. 2014).

Tanzer, A., et al., "RNA Modifications in Structure Prediction—Status Quo and Future Challenges," Methods 156:32-39, Academic Press, (Mar. 2019).

Thommen, D.S. and Schumacher, T.N., "T Cell Dysfunction in Cancer," Cancer Cell 33(4):547-562, Cell Press, United States (Apr. 2018).

Tian, N., et al., "A Structural Determinant Required for RNA Editing," Nucleic Acids Research 39(13):5669-5681, Oxford University Press, United Kingdom (Jul. 2011).

Turunen, "Axiomer Technology. Therapeutic Oligonucleotides for Directing Site-specific A-to- I Editing by Endogenous ADAR Enzymes," (Retrieved from https://www.proqr.com/wp-content/uploads/downloads/2017/11/Axiomer%20technology%20OTS%20170921.pdf), 22 pages, Sep. 25, 2017.

Tzeng, H.T., et al., "PD-1 Blockage Reverses Immune Dysfunction and Hepatitis B Viral Persistence in a Mouse Animal Model," PloS one 7(6):e39179, Public Library of Science, United States (Jun. 2012).

UK Search Report Issued in Application No. GB1905732.2, Aug. 23, 2019, 4 pages.

Urbani, S., et al., "PD-1 Expression in Acute Hepatitis C Virus (HCV) Infection is Associated with HCV-specific CD8 Exhaustion," Journal of Virology 80(22):11398-11403, American Society for Microbiology, United States (Nov. 2006).

Velu, V., et al., "Enhancing SIV-specific Immunity in vivo by PD-1 Blockade," Nature 458(7235):206-210, Nature Publishing Group, United Kingdom (Mar. 2009).

Vogel, P., et al., "Improving Site-directed RNA Editing in Vitro and in Cell Culture by Chemical Modification of the GuideRNA," Angewandte Chemie 53(24):6267-6271, Wiley-VCH, Germany (Jun. 2014).

Woolf, T. M., et al., "Toward the Therapeutic Editing of Mutated RNA Sequences, " Proc Natl Acad Sci USA 92(18):8298-8302, National Academy of Sciences, United States (Aug. 1995).

Zheng, M., et al., "Functional Exhaustion of Antiviral Lymphocytes in COVID-19 Patients," Cellular and Molecular Immunology 17(5):533-535, Chinese Society of Immunology, China (May 2020).

Zhou, P., et al., "Geometric Characteristics of Hydrogen Bonds Involving Sulfur Atoms in Proteins," Proteins 76(1):151-163, Wiley-Liss, United States (Jul. 2009).

Glen Research, "Phosphonoacetate (PACE) Oligonucleotides," Glen Report 20.21 20(2):1-16, GlenResearch.com, accessed at URL:[https://www.glenresearch.com/media/contentmanager/content/glenreport/GR20-2.pdf], Glen Research and Maravai LifeSciences, United States (Oct. 2008).

\* cited by examiner

Overview Rp

5' G A G A C C U C U G C C A G A G U U G U U C U C 3'

Overview Sp

5' G A G A C C U C U G C C A G A G U U G U U C U C 3'

○ tolerated
● disallowed

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial sequence
<220> FEATURE:
<223> OTHER INFORMATION: RNA editing oligonucleotide

<400> SEQUENCE: 1
gagaccucug cccagaguug uucuc                                         25

<210> SEQ ID NO 2
<211> LENGTH: 11
<212> TYPE: DNA
<213> ORGANISM: Artificial sequence
<220> FEATURE:
<223> OTHER INFORMATION: RNA editing oligonucleotide

<400> SEQUENCE: 2
cugcccagag u                                                        11
```

STEREOSPECIFIC LINKAGES IN RNA EDITING OLIGONUCLEOTIDES

RELATED APPLICATIONS

This application is a § 371 National Stage Application of PCT/EP2019/062163, filed May 13, 2019, which claims priority to and the benefit of United Kingdom patent application No. 1808146.3, filed May 18, 2018, the entire disclosures of each of which are incorporated herein by reference for all purposes.

FIELD OF THE INVENTION

The invention relates to the field of medicine. More in particular, it relates to the field of nucleic acid editing, whereby a nucleic acid molecule in a cell is targeted by an antisense oligonucleotide to specifically change a target nucleotide, including the correction of a mutation in the nucleic acid sequence by an enzyme having deaminase activity. More specifically, the invention relates to antisense oligonucleotides that comprise one or more internucleosidic linkages that display chirality and wherein the antisense oligonucleotides are optimized by inserting stereospecific variants at selected positions, preferably to increase enzyme engagement and nucleic acid editing efficiency.

BACKGROUND OF THE INVENTION

RNA editing is a natural process through which eukaryotic cells alter the sequence of their RNA molecules, often in a site-specific and precise way, thereby increasing the repertoire of genome encoded RNAs by several orders of magnitude. RNA editing enzymes have been described for eukaryotic species throughout the animal and plant kingdoms, and these processes play an important role in managing cellular homeostasis in metazoans from the simplest life forms (such as *Caenorhabditis elegans*) to humans. Examples of RNA editing are adenosine (A) to inosine (I) conversions and cytidine (C) to uridine (U) conversions, which occur through enzymes called adenosine deaminase and cytidine deaminase, respectively. The most extensively studied RNA editing system is the adenosine deaminase enzyme.

Adenosine deaminase is a multi-domain protein, comprising a catalytic domain, and two to three double-stranded RNA recognition domains, depending on the enzyme in question. The recognition domain recognizes a specific double stranded RNA (dsRNA) sequence and/or conformation, whereas the catalytic domain converts an adenosine (A) into inosine (I) in a nearby, more or less predefined, position in the target RNA, by deamination of the nucleobase. Inosine is read as guanine by the translational machinery of the cell, meaning that, if an edited adenosine is in a coding region of an mRNA or pre-mRNA, it can recode the protein sequence. A to I conversions may also occur in 5' non-coding sequences of a target mRNA, creating new translational start sites upstream of the original start site, which gives rise to N-terminally extended proteins, or in the 3' UTR or other non-coding parts of the transcript, which may affect the processing and/or stability of the RNA. In addition, A to I conversions may take place in splice elements in introns or exons in pre-mRNAs, thereby altering the pattern of splicing. As a result thereof, exons may be included or skipped. The adenosine deaminases are part of a family of enzymes known as Adenosine Deaminases acting on RNA (ADAR), including human deaminases hADAR1, hADAR2 and hADAR3.

The use of oligonucleotides to edit a target RNA applying adenosine deaminase has been described (e.g. Montiel-Gonzalez et al. PNAS 2013, 110 (45): 18285-18290; Vogel et al. 2014. Angewandte Chemie Int Ed 53:267-271; Woolf et al. 1995. PNAS 92:8298-8302). Montiel-Gonzalez et al. (2013) described the editing of a target RNA using a genetically engineered fusion protein, comprising an adenosine deaminase domain of the hADAR2 protein fused to a bacteriophage lambda N protein, which recognises the boxB RNA hairpin sequence. The natural dsRNA binding domains of hADAR2 had been removed to eliminate the substrate recognition properties of the natural ADAR and replace it by the boxB recognition domain of lambda N-protein. The authors created an antisense oligonucleotide comprising a 'guide RNA' (gRNA) part that is complementary to the target sequence for editing, fused to a boxB portion for sequence specific recognition by the N-domain-deaminase fusion protein. By doing so, it was elegantly shown that the guide RNA oligonucleotide faithfully directed the adenosine deaminase fusion protein to the target site, resulting in guide RNA-directed site-specific A to I editing of the target RNA. These guide RNAs are longer than 50 nucleotides, which is generally too long for therapeutic applications, because of difficulties in manufacturing and limited cell entry. A disadvantage of this method in a therapeutic setting is also the need for a fusion protein consisting of the boxB recognition domain of bacteriophage lambda N-protein, genetically fused to the adenosine deaminase domain of a truncated natural ADAR protein. It requires target cells to be either transduced with the fusion protein, which is a major hurdle, or that target cells are transfected with a nucleic acid construct encoding the engineered adenosine deaminase fusion protein for expression. The latter requirement constitutes no minor obstacle when editing is to be achieved in a multicellular organism, such as in therapy against human disease to correct a genetic disorder.

Vogel et al. (2014) disclosed editing of RNA coding for eCFP and Factor V Leiden, using a benzylguanine substituted guide RNA and a genetically engineered fusion protein, comprising the adenosine deaminase domains of ADAR1 or ADAR2 (lacking the dsRNA binding domains) genetically fused to a SNAP-tag domain (an engineered O6-alkylguanine-DNA-alkyl transferase). Although the genetically engineered artificial deaminase fusion protein could be targeted to a desired editing site in the target RNAs in Hela cells in culture, through its SNAP-tag domain which is covalently linked to a guide RNA through a 5'-terminal O6-benzylguanine modification, this system suffers from similar drawbacks as the genetically engineered ADARs described by Montiel-Gonzalez et al. (2013), in that it is not clear how to apply the system without having to genetically modify the ADAR first and subsequently transfect or transduct the cells harboring the target RNA, to provide the cells with this genetically engineered protein. Clearly, this system is not readily adaptable for use in humans, e.g. in a therapeutic setting.

Woolf et al. (1995) disclosed a simpler approach, using relatively long single stranded antisense RNA oligonucleotides (25-52 nucleotides in length) wherein the longer oligonucleotides (34-mer and 52-mer) could promote editing of the target RNA by endogenous ADAR because of the double stranded nature of the target RNA and the oligonucleotide hybridizing thereto. The oligonucleotides of Woolf et al. (1995) that were 100% complementary to the target RNA sequences only appeared to function in cell extracts or in amphibian (*Xenopus*) oocytes by microinjection, and suffered from severe lack of specificity: nearly all adenosines in the target RNA strand that was complementary to the antisense oligonucleotide were edited. An oligonucleotide, 34 nucleotides in length, wherein each nucleotide carried a 2'-O-methyl modification, was tested and shown to be inactive in Woolf et al. (1995). In order to provide stability against nucleases, a 34-mer RNA, modified with 2'-O-methyl-modified phosphorothioate nucleotides at the 5'- and 3'-terminal 5 nucleotides, was also tested. It was shown that the central unmodified region of this oligonucleotide could promote editing of the target RNA by endogenous ADAR, with the terminal modifications providing protection against exonuclease degradation. Woolf et al. (1995) does not achieve deamination of a specific target adenosine in the target RNA sequence. As mentioned, nearly all adenosines opposite an unmodified nucleotide in the antisense oligonucleotide were edited (therefore nearly all adenosines opposite nucleotides in the central unmodified region, if the 5'- and 3'-terminal 5 nucleotides of the antisense oligonucleotide were modified, or nearly all adenosines in the target RNA strand if no nucleotides were modified).

It is known that ADAR may act on any dsRNA. Through a process sometimes referred to as 'promiscuous editing', the enzyme will edit multiple A's in the dsRNA. Hence, there is a need for methods and means that circumvent such promiscuous editing and that only target specified adenosines in a target RNA sequence for therapeutic applicability. Vogel et al. (2014) showed that such off-target editing can be suppressed by using 2'-O-methyl-modified nucleotides in the oligonucleotide at positions opposite to the adenosines that should not be edited, and use a non-modified nucleotide directly opposite to the specifically targeted adenosine on the target RNA. However, the specific editing effect at the target nucleotide has not been shown to take place in that article without the use of recombinant ADAR enzymes that have covalent bonds with the antisense oligonucleotide.

WO 2016/097212 discloses antisense oligonucleotides (AONs) for the targeted editing of RNA, wherein the AONs are characterized by a sequence that is complementary to a target RNA sequence (therein referred to as the 'targeting portion') and by the presence of a stem-loop structure (therein referred to as the 'recruitment portion'), which is preferably non-complementary to the target RNA. Such oligonucleotides are referred to as 'self-looping AONs'. The recruitment portion acts in recruiting a natural ADAR enzyme present in the cell to the dsRNA formed by hybridization of the target sequence with the targeting portion. Due to the recruitment portion there is no need for conjugated entities or presence of modified recombinant ADAR enzymes. WO 2016/097212 describes the recruitment portion as being a stem-loop structure mimicking either a natural substrate (e.g. the GluB receptor) or a Z-DNA structure known to be recognized by the dsRNA binding regions of ADAR enzymes. A stem-loop structure can be an intermolecular stem-loop structure, formed by two separate nucleic acid strands, or an intramolecular stem loop structure, formed within a single nucleic acid strand. The stem-loop structure of the recruitment portion as described in WO 2016/097212 is an intramolecular stem-loop structure, formed within the AON itself, and able to attract ADAR.

WO 2017/220751 and WO 2018/041973 describe AONs that do not comprise a recruitment portion but that are (almost fully) complementary to the targeted area, except for one or more mismatches, or so-called 'wobbles' or bulges. The sole mismatch may be the nucleotide opposite the target adenosine, but in other embodiments AONs are described that have multiple bulges and/or wobbles when attached to the target sequence area. It appeared that it was possible to achieve in vitro, ex vivo and in vivo RNA editing with AONs lacking a recruitment portion and with endogenous ADAR enzymes when the sequence of the AON was carefully selected such that it could attract ADAR. The nucleotide in the AON directly opposite the target adenosines was described as not carrying a 2'-O-methyl modification. It could also be a DNA nucleotide, wherein the remainder of the AON was carrying 2'-O-alkyl modifications at the sugar entity (such as 2'-O-methyl), or the nucleotides within the so-called 'Central Triplet' or directly surrounding the Central Triplet contained particular chemical modifications (or were DNA) that further improved the RNA editing efficiency and/or increased the resistance against nucleases. Such effects could even be further improved when using sense oligonucleotides (SONs) that 'protect' the AONs against breakdown (described in PCT/EP2018/051202, unpublished).

It is further noted that yet another editing technique exists which uses oligonucleotides, known as the CRISPR/Cas9 system. However, this editing complex acts on DNA. It also suffers from the same drawback as the engineered ADAR systems described above, because it requires co-delivery to the target cell of the CRISPR/Cas9 enzyme, or an expression construct encoding the same, together with the guide oligonucleotide. Several investigators are experimenting with base editing of DNA sequences, for example by employing fusion proteins comprising Cas9 and enzymes with deaminase activity that are guided to the DNA target site by guide RNAs that are designed in accordance with the CRISPR/Cas9 target finding rules.

Despite the achievements outlined above, there remains a need for new compounds that can utilise (endogenous) cellular pathways and enzymes that have deaminase activity, such as naturally expressed ADAR enzymes to more specifically and more efficiently edit endogenous nucleic acids in mammalian cells, even in whole organisms, to alleviate disease.

SUMMARY OF THE INVENTION

The present invention relates to an oligonucleotide composition capable of forming a double stranded complex with a target nucleic acid molecule in a cell, and capable of recruiting an enzyme with nucleotide deaminase activity, wherein the target nucleic acid molecule comprises a target nucleotide for deamination by the enzyme with nucleotide deamination activity, wherein the oligonucleotide comprises a position opposite the target nucleotide that mismatches with the target nucleotide, characterized in that the oligonucleotide comprises at least one internucleotide linkage which is enriched for one stereospecific configuration. Preferably, the oligonucleotide comprises at least one internucleotide linkage with predominantly an Rp configuration and at least one internucleotide linkage with predominantly an Sp configuration. In another preferred aspect, the oligonucleotide comprises at least one internucleotide linkage without a phosphorothioate modification. Preferably, the enzyme with nucleotide deaminase activity is ADAR1 or ADAR2. Also preferred is an oligonucleotide composition according to the invention, wherein the target nucleotide is an adenosine that is deaminated to an inosine, which is being read as a guanine by the translation machinery. The invention also relates to a pharmaceutical composition comprising the oligonucleotide as characterized herein, and a pharmaceutically acceptable carrier.

In another aspect the invention relates to an (editing) oligonucleotide (EON) capable of forming a double stranded complex with a target RNA molecule in a cell, and capable of recruiting an endogenous enzyme with ADAR activity, wherein the target RNA molecule comprises a target adenosine for deamination by the enzyme with ADAR activity, wherein the EON comprises a Central Triplet of three sequential nucleotides in which the nucleotide directly opposite the target adenosine is the middle nucleotide (position 0) of the Central Triplet and wherein the positions are positively (+) and negatively (−) incremented towards the 5' and 3' ends of the EON, respectively, wherein the EON comprises a nucleotide at position 0 that mismatches with the target adenosine. In yet another aspect, the invention relates to an EON according to the invention for use in the treatment or prevention of a genetic disorder. The invention also relates to a method for the deamination of at least one target adenosine present in a target RNA molecule in a cell, the method comprising the steps of providing the cell with an EON according to the invention, allowing uptake by the cell of the EON, allowing annealing of the EON to the target RNA molecule, allowing a mammalian enzyme with ADAR activity to deaminate the target adenosine in the target RNA molecule to an inosine; and optionally identifying the presence of the inosine in the target RNA.

DETAILED DESCRIPTION OF THE INVENTION

Figure 1:
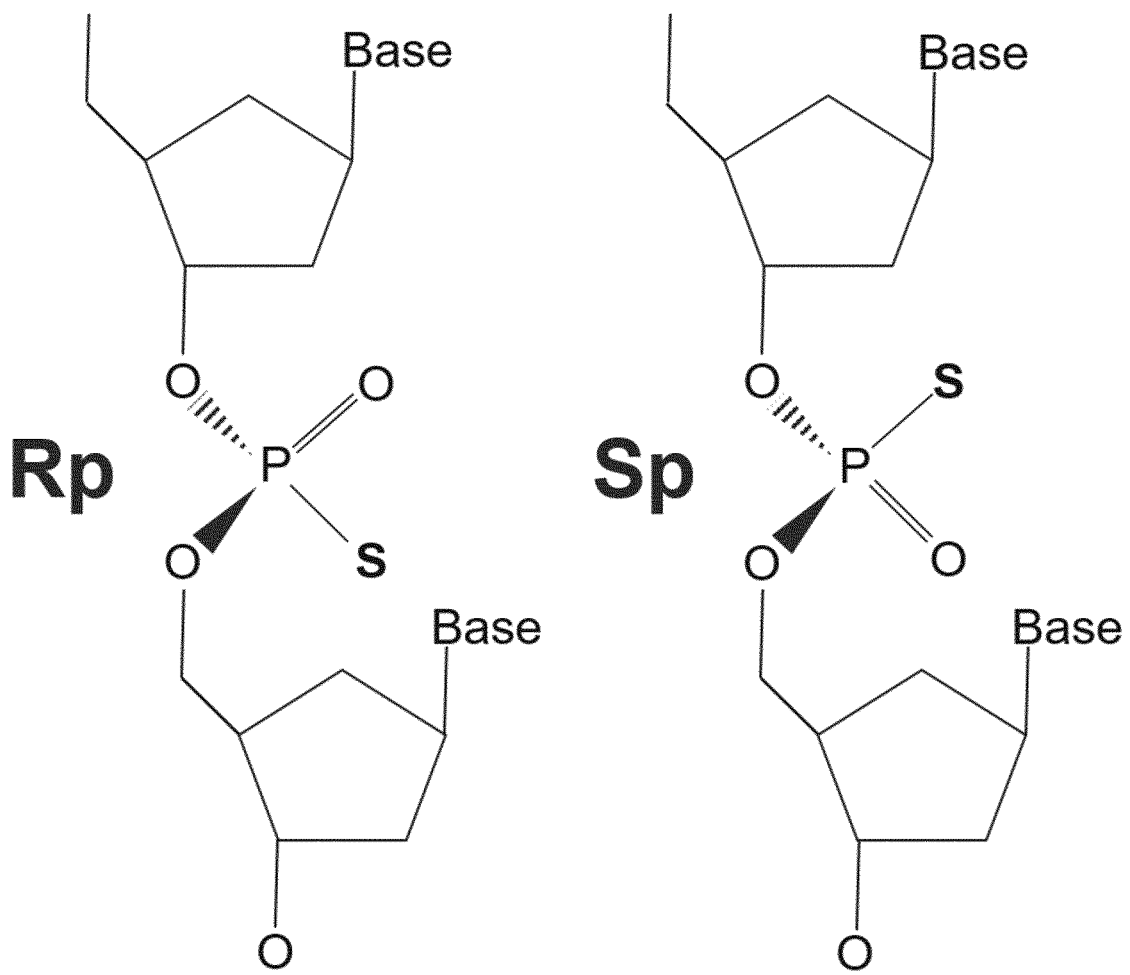
FIG. 1 is a representation of the Rp and Sp stereospecific configurations for phosphorothioate linkages.

There is a constant need for improving the pharmacokinetic properties of (RNA) editing oligonucleotides (EONs) without negatively affecting editing efficiency of the target adenosine in the target RNA. Many chemical modifications exist in the generation of antisense oligonucleotides, whose properties are incompatible with the desire of designing effective editing oligonucleotides. In the search for better pharmacokinetic properties, previously it was found that a 2'-O-methoxyethyl (2'-MOE) modification of the ribose of some, but not all, nucleotides-surprisingly-appeared compatible with efficient ADAR engagement and editing (GB 1802392.9 unpublished). Examples of enhanced pharmacokinetic properties are cellular uptake and intracellular trafficking, stability and so on. Whereas the properties of 2'-MOE modifications were known as such, the compatibility thereof with ADAR engagement and deamination was not known. The positions inside the oligonucleotide where 2'-MOE is compatible with ADAR and where it is not were unraveled.

In a further attempt to improve oligonucleotide properties as guides for targeted base editing, such as deamination, more in particular deamination by enzymes having adenosine deaminase activity, the inventors interrogated oligonucleotides with regard to the tolerability of different internucleosidic linkages. More in particular, the present inventors looked at internucleosidic linkages which possess a chiral centre, such as a chiral phosphonate centre. More in particular, the inventor asked where in the oligonucleotide phosphorothioate linkages are tolerated and, if so, if controlling chirality in particular positions where phosphorothioate is tolerated improves the hydrogen bonding interaction between the internucleosidic linkage and those amino acid residues of the enzyme having deamination activity that interact with the oligonucleotide when forming a helical complex with the target nucleic acid. In the following sections, a more detailed description of the findings and conclusions will be presented based on the interaction of chemically modified EONs designed to bind the target RNA at the target site surrounding a target adenosine, recruiting an adenosine deaminase acting on RNA (ADAR) for deamination of the target adenosine, converting it into an inosine. It should, however, be clear that the invention is not limited to oligonucleotides or methods designed to recruit ADAR to convert target adenosine into inosines. It should be understood, that the invention encompasses any oligonucleotide that can bind to a target nucleic acid, recruit any protein (naturally expressed proteins as well as foreign proteins, including fusion proteins of different or the same origin) with nucleotide (including adenosine and cytidine) deamination activity, as long as at least one internucleosidic linkage comprises a chiral center (including X-phosphonate moieties, wherein X may be alkyl, alkoxy, aryl, alkylthio, acyl, —$NR^1R^1$, alkenyloxy, alkynyloxy, alkenylthio, alkynylthio, —S—$Z^+$, —Se—$Z^+$, or —$BH_3$—$Z^+$, and wherein $R^1$ is independently hydrogen, alkyl, alkenyl, alkynyl, or aryl, and wherein $Z^+$ is ammonium ion, alkylammonium ion, heteroaromatic iminium ion, or heterocyclic iminium ion, any of which is primary, secondary, tertiary or quaternary, or Z is a monovalent metal ion. Both the determination of the tolerability of such linkages per se, using computational modelling, as well as the determination of the preferred Sp or Rp stereomer of that linkage comprising a chiral centre forms part of the invention.

The present invention, in a particular aspect, relates to an oligonucleotide comprising nucleotides that are linked by internucleosidic linkages, at least one of which displays chirality, wherein said oligonucleotide—when forming a double stranded nucleic acid structure by binding to a complementary nucleic acid sequence—is capable of recruiting an enzyme with nucleotide deaminase activity on a target nucleotide in said complementary nucleic acid sequence, characterized in that said oligonucleotide has been optimized for hydrogen interactions between at least one of said internucleosidic linkages of said oligonucleotide and said enzyme having nucleotide deaminase activity. Chirality is defined as having the possibility of having stereo isomers. The present invention is about chiral control of an internucleotide linkage with chirality in an oligonucleotide that interacts with an enzyme having nucleotide deaminase activity. In one aspect of the invention, it relates to an oligonucleotide (composition) wherein the oligonucleotide has been optimized for hydrogen interaction by placing at least one internucleosidic linkage which displays chirality in a position where it does not negatively influence hydrogen interaction with the enzyme having nucleotide deaminase activity. In a preferred aspect, the oligonucleotide has been optimized for hydrogen interaction by selecting a stereospecific form of the internucleosidic linkage in one or more positions that favour the most stable hydrogen interaction with the enzyme having nucleotide deaminase activity.

The inventors of the present invention asked themselves whether the stereo specificity of the phosphorothioate linkage between nucleotides within an oligonucleotide would influence the pharmacokinetic properties and/or RNA editing efficiency of such oligonucleotides. That is the subject of the present invention. The findings as disclosed herein can, in principle, be used with any form of base editing employing synthetic oligonucleotides involving ADAR or ADAR deaminase domains, be they natural or recombinant, truncated or full length, fused to other proteins or not (e.g. Stafforst and Schneider, 2012, Angew Chem Int 51:11166-11169; Schneider et al. 2014, Nucleic Acids Res 42: e87; Montiel-Gonzalez et al. 2016, Nucleic Acids Res 44: e157).

The present invention also relates to an internucleotide linkage with the following two stereoisomeric forms Rp and Sp:

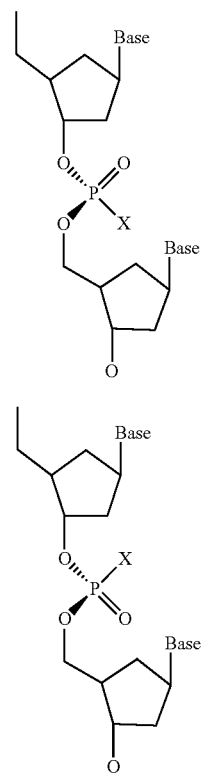

Formula I (Rp) and II (Sp),
wherein X is alkyl, alkoxy, aryl, alkylthio, acyl, —$NR^1R^1$, alkenyloxy, alkynyloxy, alkenylthio, alkynylthio, —S—$Z^+$, —Se—$Z^+$, or —$BH_3$—$Z^+$, and wherein $R^1$ is independently hydrogen, alkyl, alkenyl, alkynyl, or aryl, and wherein $Z^+$ is ammonium ion, alkylammonium ion, heteroaromatic iminium ion, or heterocyclic iminium ion, any of which is primary, secondary, tertiary or quaternary, or Z is a monovalent metal ion.

The invention further relates to an oligonucleotide according to the invention, wherein the internucleosidic linkage that displays chirality is a phosphorotioate linkage. In a preferred embodiment, the enzyme with nucleoside deaminase activity comprises an ADAR2 deaminase domain or a mutant or derivative thereof or fusion protein therewith. In yet another preferred embodiment the invention relates to an oligonucleotide, wherein the oligonucleotide has been optimized in 2, 3, 4, 5, 6, 7, 8, 9 or 10 internucleosidic linkages. In a further preferred aspect, the oligonucleotide comprises 2, 3, 4, 5, 6, 7, 8, 9 or 10 stereospecific internucleosidic linkages displaying chirality.

In vitro studies have shown that the properties of antisense nucleotides such as binding affinity, sequence specific binding to the complementary RNA, and stability to nucleases are affected by the configurations of the phosphorous atoms. WO 2010/064146 discloses methods of stereocontrolled syntheses of phosphorous atom-modified nucleic acids comprising chiral X-phosphonate moieties.

Figure 2:
FIG. 2 shows the result of the computationally-guided analysis, as described herein, showing the nucleotides of a 25 nt-long region from the IDUA-RNA targeting EON. The EON sequence is provided from 5' to 3' (SEQ ID NO:1). For each connection, a structural evaluation was performed of the compatibility of Rp and Sp phosphorothioate linkages insertions with the conservation of the potential hydrogen bond network mediated by the EON oxygen-phosphate backbone. The open circles characterize the nucleotides where Rp or Sp phosphorothioate linkages are tolerated. The black circles indicate positions where phosphorothioate should be excluded.
Figure 2:
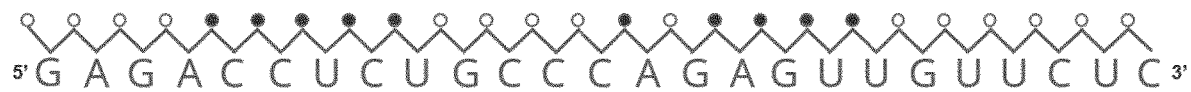

Chemically modified oligonucleotides used for therapeutics applications often carry phosphorothioate linkages (herein and elsewhere often abbreviated as PS). The most important role of this modification is to protect the polymer from nuclease-mediated degradation. It inhibits exonuclease degradation at RNA ends and internally limits the attack of endonucleases. Remarkably, it has been reported that PS-rich oligonucleotides have greater affinity for proteins (Brown D. A. et al., Effect of phosphorothioate modifications of oligodeoxynucleotides on specific protein binding, J Biol Chem, 1994; Antisense Drug Technology, Principles, Strategies, and Applications, Second Edition, 2007, edited by Stanley T. Crooke). However, such binding is most probably mediated by non-specific contacts. In biological molecules the substitution of the oxygen-phosphate by a sulfur-phosphate linkage may interfere with intermolecular hydrogen bond network established in natural protein/RNA complexes. Indeed, studies demonstrated that sulfur atoms are very poor hydrogen bond acceptors but moderately good hydrogen bond donors (Zhou et al. Geometric characteristics of hydrogen bonds involving sulfur atoms in proteins, Proteins, 2009). However, in protein structures the sulfur atom of methionine and cysteine has been reported to be a hydrogen acceptor (Singleton et al. X-ray structure of pyrrolidone carboxyl peptidase from the hyperthermophilic archaeon *Thermococcus litoralis*, Structure, 1999; Diaz et al. Unusual Cys-Tyr covalent bond in a large catalase, J. Mol. Biol., 2004). Although theoretical studies and several experimental data validate the existence of OH . . . S and NH . . . S hydrogen bonds, the sulfur electronegativity is lower compared to oxygen. In addition to the fact that the relative angle between two polar groups defines the bond strength, the inventors of the present invention considered in their approach that electronegativity is a major parameter for hydrogen bonds formation. Thus, for this structure-based oligonucleotide design, it was assumed that potential hydrogen bond contacts between the EON oxygen-phosphate backbone and the ADAR2 deaminase domain side-chains should be preserved. The inventors of the present invention propose that these connections better support the interaction between the two molecular partners. Stereospecific phosphorothioate linkages show high potential to fine-tune the interaction between an enzyme and its ligand. Indeed, a stereochemical code has been recently highlighted based on structural data collected on the bound RNase H1 and coupled to the analysis of mipomersen-derived oligonucleotide sequences (Iwamoto et al. 2017. Nat Biotechnol 35:845-851). These oligonucleotides bearing the mipomersen primary sequence are composed of pure or combined stereospecific phosphorothioate linkages designated Rp and Sp (FIG. 1). The authors demonstrated for their ASO gapmers that Sp linkages increase lipophilicity and stability in vitro. Concomitantly, they reported that ASO gapmers with stereochemically-controlled PS configurations modulate potency and biological half-life. Finally, they optimized the stereospecificity of a PS linkages triplet interacting with RNase H1 side-chains leading to a significant improvement of enzymatic activity. Their results confirm the importance of stereospecific PS linkages for physicochemical and pharmacologic features of therapeutics oligonucleotides. To take advantage of this new type of chemistry, the inventors of the present invention decided to insert stereospecific phosphorothioate linkages in their computationally-guided approach for EON design. The goal was to monitor the compatibility between the insertion of stereospecific PS linkages and the preservation of potential intermolecular hydrogen bond contacts involving the ADAR2 deaminase side-chains and the EONs oxygen-phosphate backbone. For this, the in silico modelling with the published RNA-bound ADAR2 deaminase structure (Matthews et al. 2016. Nat Struct Mol Biol 23:426-433) was initiated and an intra and intermolecular network of distances was generated that is required for de novo structure calculation. Specific libraries including the Rp and Sp stereochemical configurations were created for the calculation software. CYANA3.0 which combined simulated annealing with molecular dynamics in torsion angle space (Güntert P et al, *J. Mol. Biol*, 1997) allowed the calculation of protein-RNA ensembles. These complexes were composed of the ADAR2 deaminase domain bound to a double-stranded RNA that is formed by the chemically-modified EON annealed to the IDUA target sequence. For each phosphorothioate linkage of a 25nt-long EON spanning the ADAR2 deaminase binding interface, the Rp and the Sp configuration was successfully introduced. For each configuration, 200 protein-RNA complexes were calculated and the 20-lowest structures were selected for subsequent refinement using the restrained molecular dynamics of the AMBER16 package. In total, 10,000 structures were calculated and the 1000 most energetically favourable ones were analysed. As mentioned previously, the structural study determined whether the Rp and the Sp phosphorothioate linkages are tolerated in the EON, without altering the potential hydrogen bond contacts between the oxygen-phosphate backbone and the ADAR2 deaminase side-chains (FIG. 2). For some positions, it was concluded that phosphorothioate linkages are not compatible with the preservation of the most stable hydrogen bond network (oxygen-mediated). This in fact means that it is preferred that at those positions no phosphorothioate modification is present. However, such should be balanced against the potential risk of instability when an EON is not fully covered with internucleotides carrying a phosphorothioate modification. It is to be understood that the positions found to be preferred for Rp, Sp, or any of these two, or on the other hand positions that should not have a PS at all, are applicable for any given EON, irrespective of the nucleotide sequence. Hence, where as exemplified herein an IDUA targeting EON sequence was used, the teaching of the positions is applicable to any given EON sequence, targeting any other kind of target sequence. Clearly, as outlined herein, modelling was performed with ADAR2 as the enzyme with deaminase activity and the person skilled in the art would understand that outcomes may change when the EON is modelled with other deaminase activity bearing enzymes.

The method allowed the inventors to highlight a pattern of stereospecific phosphorothioate linkages compatible with an optimized intermolecular hydrogen bond network between the deaminase domain of the enzyme with ADAR activity (preferably ADAR2) and the EON. The structurally-based stereochemical code is provided in FIG. 3. To alleviate ambiguities regarding the position of the phosphorothioate linkage relative to its nucleoside, the selected nomenclature within an extended region of the EON are provided in detail in FIG. 3. Notably, in FIG. 3 the nucleotide opposite the target adenosine in the target sequence is given as the "0" nucleotide position, while the "0" position for the linkage numbering is shifted halfway between nucleotides towards the 5' end.

The present invention relates to an oligonucleotide composition capable of forming a double stranded complex with a target nucleic acid molecule in a cell, and capable of recruiting an enzyme with nucleotide deaminase activity, wherein the target nucleic acid molecule comprises a target nucleotide for deamination by the enzyme with nucleotide deamination activity, wherein the oligonucleotide comprises a position opposite the target nucleotide that mismatches with the target nucleotide, characterized in that the oligonucleotide comprises at least one internucleotide linkage which is enriched for one stereospecific configuration. The skilled person is aware of a variety of enzymes that have nucleotide deaminase activity, such as ADAR1, ADAR2, APOBEC, Cas13 and the like. The invention, albeit modelled with ADAR2 nucleotide deaminase domain, is not restricted thereto, as the teaching of the current disclosure makes that the skilled person can model the stereospecificity for any (editing) oligonucleotide towards any enzyme with nucleotide deaminase activity it interacts with. The skilled person is also aware of a variety of internucleosidic linkages that display chirality, such as boranophosphates, phosphoroselenoate and some alkyl-substituted phosphonates (alkylphosphonates) that are all part of the invention. In a preferred embodiment, the 'stereospecific purity' of the composition is 60%, more preferably 70%, even more preferably 80% and most preferably 90% or higher. Preferably, the oligonucleotide comprises at least one internucleotide linkage with predominantly an Rp configuration and at least one internucleotide linkage with predominantly an Sp configuration. More preferably, the oligonucleotide comprises at least one internucleotide linkage without a phosphorothioate modification. In yet another aspect, the oligonucleotide comprises one or more nucleotides comprising a 2'-O-methoxyethyl (2'-MOE) ribose modification; wherein the oligonucleotide comprises one or more nucleotides not comprising a 2'-MOE ribose modification, and wherein the 2'-MOE ribose modifications are at positions that do not prevent the enzyme with nucleotide deaminase activity from deaminating the target nucleotide. And in another preferred aspect, the oligonucleotide comprises 2'-O-methyl (2'-OMe) ribose modifications at the positions that do not comprise a 2'-MOE ribose modification, and/or wherein the oligonucleotide comprises deoxynucleotides at positions that do not comprise a 2'-MOE ribose modification. In all aspects of the invention, the enzyme with nucleotide deaminase activity is preferably ADAR1 or ADAR2. In yet another preferred aspect, the oligonucleotide is at least 10, 11, 12, 13, 14, 15, 16 or 17 nucleotides in length, and also the oligonucleotide is shorter than 100 nucleotides, preferably shorter than 60 nucleotides. In a highly preferred aspect, the oligonucleotide is an RNA editing oligonucleotide that targets a pre-mRNA or an mRNA, wherein the target nucleotide is an adenosine in the target RNA, wherein the adenosine is deaminated to an inosine, which is being read as a guanine by the translation machinery. In a further preferred aspect, the adenosine is located in a UGA or UAG stop codon, which is edited to a UGG codon; or wherein the two target nucleotides are the two adenosines in a UAA stop codon, which codon is edited to a UGG codon through the deamination of both target adenosines, wherein two nucleotides in the oligonucleotide mismatch with the target nucleic acid. The invention also relates to a pharmaceutical composition comprising the oligonucleotide as characterized herein, and a pharmaceutically acceptable carrier.

The invention relates to an editing oligonucleotide (EON) capable of forming a double stranded complex with a target RNA molecule in a cell, and capable of recruiting an endogenous enzyme with ADAR activity, wherein the target RNA molecule comprises a target adenosine for deamination by the enzyme with ADAR activity, wherein the EON comprises at least one internucleotide phosphorothioate linkage with predominantly an Rp configuration or predominantly an Sp stereospecific configuration. It was found that certain positions preferably carry an Rp configuration, whereas other positions preferably carry an Sp configuration. Also, it was found that at some positions, it did not matter which of the two configurations should be present, as either of the two could be introduced. On the other hand, it was also found that at certain positions it was in fact preferred that no phosphorothioate modification should be introduced as it would hamper the EON-protein interaction, with either the Rp or Sp configuration. Notably, as indicated herein, phosphorothioate modifications are generally introduced to prevent breakdown (and there through increase RNA editing efficiency). The skilled person understands that this introduces a sort of balance between better or weaker interaction between EON and ADAR enzyme on the one hand, and on the other hand increased or decreased stability of the EON in vivo. The skilled person is capable of using methodology in vitro as well as in vivo to determine which of the positions should or should not carry a phosphorothioate modification to obtain the most efficient RNA editing outcome. This determination is clearly based on the sequence of the EON itself and the target sequence, possibly the structure of the pre-mRNA, the enzyme with ADAR activity that appears to be used (ADAR 1 or ADAR2), the cell in which the RNA editing should occur, etc. The present invention provides the tools for the skilled person to apply this method and to make that determination for each possible EON that can be used for any disease that could potentially be targeted by an EON.

Preferably, the EON according to the invention comprises nucleotides carrying a 2'-MOE ribose modification and, even more preferably, a 2'-O-methyl (2'-OMe) ribose modification at the positions that do not have a 2'-MOE ribose modification. As outlined herein (FIG. 3), the EON comprises a nucleotide directly opposite the target adenosine which is referred to as position 0 of the EON nucleotide sequence. Preferably, the EON comprises one or two deoxynucleotides (DNA) at positions-1 and/or 0, wherein the positions are positively (+) and negatively (−) incremented towards the 5' and 3' ends of the EON, respectively. In a preferred aspect, the EON does not comprise a 2'-MOE modification at position-1 and or 0. More preferably, the EON of the invention does not comprise a 2'-MOE modification at position +6, +1, 0, −1, −2, −3, −4, and/or −5. The enzyme with ADAR activity is an enzyme that is capable of deaminating a target adenosine in a double stranded RNA complex into an inosine. Preferably the enzyme with ADAR activity is (human) ADAR1 or ADAR2. Also preferably, the cell is a human cell. In one preferred embodiment, the EON according to the invention is longer than 10, 11, 12, 13, 14, 15, 16 or 17 nucleotides, and preferably the EON is shorter than 100 nucleotides, more preferably shorter than 60 nucleotides.

Figure 3:
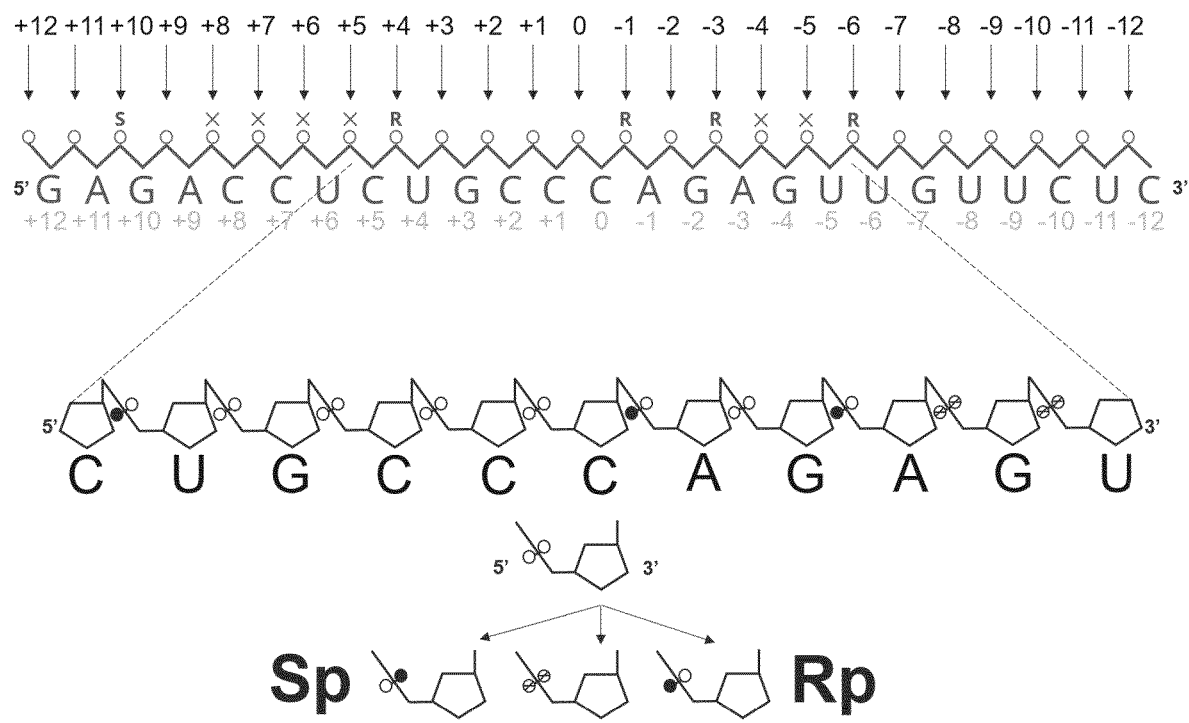
FIG. 3 shows, in the upper panel, a summary of a stereospecific phosphorothioate pattern for a region of an EON targeting an IDUA-RNA. The EON sequence is provided from 5' to 3' (SEQ ID NO: 1). Below the nucleotide sequence the order of nucleotides is given in which the "0" position refers to the nucleotide opposite the target adenosine that is to be deaminated in the target sequence. Towards the 5' end of the EON the nucleotide numbering is increasing to +12, whereas towards the 3' end of the EON the nucleotide numbering is decreasing to −12. Hence in this particular example there are 25 nucleotides shown (of a potentially longer EON). The linkage numbering is different, with the linkage 5' of a nucleotide being considered part of that nucleotide. The linkage numbering is given in the top row. As can be seen, the linkage referred to as "0" in the top row is the linkage 5' of nucleotide "0", with increasing linkage numbering towards the 5' end to +12, and with decreasing linkage numbering towards the 3' end to −12. It is to be understood that the ultimate 'linkage'+12 is not linked in this particular example, but may be linked to a next nucleotide in any given EON if it is longer at the 5' terminus. The same is true for the 3' end, where additional nucleotides may be attached. The modelling was performed with the 25 nucleotides shown, using one nucleotide (including a 5' linkage) as a so-called 'structuring modelling unit'. "R" above a linkage circle indicates the preferred Rp configuration at that position. Similarly, "S" above a linkage circle indicates the preferred Sp configuration at that position. For positions tolerating both Rp and Sp, a blank is left above the circles. A cross "X" above a circle indicates a position where phosphorothioate should be excluded/avoided. In the lower panel, a schematic view of the nucleosides with their Rp and/or Sp phosphorothioate linkages is provided. For simplicity, this view is only limited to 11 nucleotides (10 linkage positions) (SEQ ID NO:2). The black dot below the open dot represents the Rp configuration, whereas the black dot above the open dot represents the Sp configuration. Where both dots in the PS are open, both Rp and Sp are tolerated. Between nucleotides at positions −3, −4, and −5 (2 linkages) stereospecific phosphorothioates should be avoided (given by crossed dots in the PS).

FIG. 3 shows the positions of the linkages and the linkage numbering for (part of) an EON of 25 nucleotides, with linkage numbering 0 is the linkage 5' of the nucleotide referred to as 0 in the nucleotide numbering. Preferably, using this numbering for linkages, the linkages with number 0, +1, +2, +3, +9, +11, +12, −2, −7, −8, −9, −10, −11, and/or −12 do have a modification where it does not matter whether it has the Rp or Sp configuration. Also preferably, using this numbering for linkages, the linkages with number +4, −1, −3, and/or −6 preferably have the Rp configuration, while only linkage+10 preferably has a modification with the Sp configuration. Also, using this numbering for linkages, the linkages with number +5, +6, +7, +8, −4, and/or −5 preferably do not carry a (phosphorothioate) modification, but preferably have a wild type internucleotide connection. This numbering, of course as it is arbitrary chosen, but also the stereoisomeric form of the internucleotide linkage modification is irrespective of the nucleotide sequence, and applicable to any kind of EON, when interacting with ADAR2 as the preferred enzyme having deaminase activity.

The invention also relates to a pharmaceutical composition comprising the oligonucleotide according to the invention, and a pharmaceutically acceptable carrier. Suitable pharmaceutically acceptable carriers are well known to the person skilled in the art. The invention also relates to an oligonucleotide according to the invention for use in the treatment or prevention of a genetic disorder, preferably selected from the group consisting of: Cystic fibrosis, Hurler Syndrome, alpha-1-antitrypsin (A1AT) deficiency, Parkinson's disease, Alzheimer's disease, albinism, Amyotrophic lateral sclerosis, Asthma, β-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-eso1 related cancer, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, Sturge-Weber Syndrome, and cancer. The invention also relates to a use of the EON according to the invention in the manufacture of a medicament for the treatment or prevention of a genetic disorder, preferably selected from the group consisting of: Cystic fibrosis, Hurler Syndrome, alpha-1-antitrypsin (A1AT) deficiency, Parkinson's disease, Alzheimer's disease, albinism, Amyotrophic lateral sclerosis, Asthma, β-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-eso1 related cancer, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, Sturge-Weber Syndrome, and cancer.

In yet another embodiment, the invention relates to a method for the deamination of at least one target adenosine present in a target RNA molecule in a cell, the method comprising the steps of providing the cell with an EON according to the invention, allowing uptake by the cell of the EON, allowing annealing of the EON to the target RNA molecule, allowing a mammalian enzyme with ADAR activity to deaminate the target adenosine in the target RNA molecule to an inosine, and optionally identifying the presence of the inosine in the target RNA. Preferably, the presence of the inosine is detected by either (i) sequencing the target RNA sequence, (ii) assessing the presence of a functional, elongated, full length and/or wild type protein when the target adenosine is located in a UGA or UAG stop codon, which is edited to a UGG codon through the deamination, (iii) assessing the presence of a functional, elongated, full length and/or wild type protein when two target adenosines are located in a UAA stop codon, which is edited to a UGG codon through the deamination of both target adenosines, (iv) assessing whether splicing of the pre-mRNA was altered by the deamination; or (v) using a functional read-out, wherein the target RNA after the deamination encodes a functional, full length, elongated and/or wild type protein. Clearly, when two target adenosine need to be deaminated, the linkage numbering (as outlined herein for a single target adenosine) should be adjusted accordingly, although the specific stereoisomeric form of the phosphorothioate modification would not be altered in the EON itself, as that relates to the interaction with the enzyme with deaminase activity.

The antisense oligonucleotides (AONs; herein often referred to as editing oligonucleotides, or EONs) of the present invention do preferably not comprise a recruitment portion as described in WO 2016/097212. The EONs of the present invention preferably do not comprise a portion that is capable of forming an intramolecular stem-loop structure. In one embodiment, the present invention relates to EONs that target premature termination stop codons (PTCs) present in the (pre) mRNA to alter the adenosine present in the stop codon to an inosine (read as a G), which in turn then results in read-through during translation and a full length functional protein. In one particular embodiment, the present invention relates to EONs for use in the treatment of cystic fibrosis (CF), and in an even further preferred embodiment, the present invention relates to EONs for use in the treatment of CF wherein PTCs such as the G542X (UGAG), W1282X (UGAA), R553X (UGAG), R1162X (UGAG), Y122X (UAA, both adenosines), W1089X, W846X, and W401X mutations are modified through RNA editing to amino acid encoding codons, and thereby allowing the translation to full length proteins. The teaching of the present invention, the computational modelling of allowable and not-allowable positions regarding stereospecific phosphorothioate linkage modifications, as outlined herein, is applicable for all genetic diseases that may be targeted with EONs and may be treated through RNA editing. It depends on the target sequence, the applicable EON and the context of the ADAR protein to pinpoint preferred and non-preferred positions for these stereospecific modifications. This is the first time that it is shown that computational modelling can be applied to find preferred positions within therapeutic EONs that may be or should not be modified with Rp and/or Sp stereospecific phosphorothioate configuration modifications to increase the RNA editing efficiencies of such EONS.

The present invention relates to an EON for the deamination of a target adenosine in a target RNA, wherein the EON is complementary to a target RNA region comprising the target adenosine, and the EON optionally comprises one or more mismatches, wobbles and/or bulges with the complementary target RNA region; the EON comprises one or more nucleotides with one or more sugar modifications, provided that the nucleotide opposite the target adenosine comprises a ribose with a 2'—OH group, or a deoxyribose with a 2'—H group, and further wherein the EON does not have 2'-MOE modifications at certain positions relative to the nucleotide opposite the target adenosine, and further does have 2'-MOE modifications at other positions within the EON, as further defined herein. The EON does preferably not comprise a portion that is capable of forming an intramolecular stem-loop structure that is capable of binding an ADAR enzyme. The EON does preferably not include a 5'-terminal O6-benzylguanine modification. The EON preferably does not include a 5'-terminal amino modification. The EON preferably is not covalently linked to a SNAP-tag domain. In another preferred embodiment the target RNA is human CFTR. In a more preferred embodiment, the stop codon is a premature termination stop codon in the human CFTR (pre) mRNA and even more preferably selected from the group of stop codon mutations in CFTR consisting of: G542X, W1282X, R553X, R1162X, Y122X, W1089X, W846X, and W401X. More preferably, the splice mutation in human CFTR is selected from the group of consisting of: 621+1G>T and 1717-1G>A. In one aspect, the present invention relates to an EON for use in the treatment of Cystic Fibrosis, wherein the EON enables the deamination of an adenosine present in a PTC present in the CFTR (pre) mRNA and wherein the PTC results in early translation termination that eventually causes the disease.

In yet another aspect, the invention relates to an EON according to the invention capable of forming a double stranded complex with a target RNA in a cell, for use in the deamination of a target adenosine in a disease-related splice mutation present in the target RNA, wherein the nucleotide in the EON that is opposite the target adenosine does not carry a 2'-O-methyl (2'-OMe) modification; the nucleotide directly 5' and/or 3' from the nucleotide opposite the target adenosine carry a sugar modification and/or a base modification to render the EON more stable and/or more effective in RNA editing. In another preferred aspect the nucleotide in the EON opposite the target adenosine is not RNA but DNA, and in an even more preferred aspect, the nucleotide opposite the target adenosine as well as the nucleotide 5' and/or 3' of the nucleotide opposite the target adenosine are DNA nucleotides, while the remainder (not DNA) of the nucleotides in the EON are preferably 2'-O-alkyl modified ribonucleotides. When two nucleotides are DNA all others may be RNA and may be 2'-OMe or 2'-MOE modified, whereas in particular aspects the third nucleotide in the triplet opposite the target adenosine may be RNA and non-modified, as long as the nucleotide opposite the target adenosine is not 2'-OMe modified. In one particular aspect the invention relates to an EON for the deamination of a target adenosine present in the target RNA by an enzyme present in the cell (likely an ADAR enzyme), wherein the EON is (partly) complementary to a target RNA region comprising the target adenosine, wherein the nucleotide opposite the target adenosine comprises a deoxyribose with a 2'—H group, wherein the nucleotide 5' and/or 3' of the nucleotide opposite the target adenosine also comprises a deoxyribose with a 2'—H group, and the remainder of the EON comprises ribonucleosides, preferably all with 2'-OMe or 2'-MOE modifications. In the case of two sequential adenosines (e.g. in the Y122X mutation: UAA) that need to be edited, it is preferred that the nucleotides in the EON that are opposite the two adenosines do both not carry a 2'-O-methyl modification. In another preferred aspect, the EON according to the invention is not a 17-mer or a 20-mer. In yet another aspect the EON according to the invention is longer than 17 nucleotides, or shorter than 14 nucleotides. In a preferred embodiment, the EON according to the invention comprises 1, 2, 3, 4, 5, 6, 7, 8, 9 or 10 mismatches, wobbles and/or bulges with the complementary target RNA region. Preferably, the nucleotide opposite the target adenosine is a cytidine, a deoxycytidine, a uridine, or a deoxyuridine. When the nucleotide opposite the target adenosine is a cytidine or a deoxycytidine, the EON comprises at least one mismatch with the target RNA molecule. When the nucleotide opposite the target adenosine is a uridine or a deoxyuridine, the EON may be 100% complementary and not have any mismatches, wobbles or bulges in relation to the target RNA. However, in a preferred aspect one or more additional mismatches, wobbles and/or bulges are present between EON and target RNA whether the nucleotide opposite the target adenosine is a cytidine, a deoxycytidine, a uridine, or a deoxyuridine. In another preferred embodiment, the nucleotide directly 5' and/or 3' from the nucleotide opposite the target adenosine (together with the nucleotide opposite the target adenosine forming a triplet) comprises a ribose with a 2'—OH group, or a deoxyribose with a 2'—H group, or a mixture of these two (triplet consists then of DNA-DNA-DNA; DNA-DNA-RNA; DNA-RNA-DNA; DNA-RNA-RNA; RNA-DNA-DNA; RNA-DNA-RNA; RNA-RNA-DNA; or RNA-RNA-RNA; wherein the middle nucleoside does not have a 2'-O-methyl modification (when RNA) and either or both surrounding nucleosides also do not have a 2'-O-methyl modification). It is then preferred that all other nucleotides in the EON then do have a 2'-O-alkyl group, preferably a 2'-O-methyl group, or a 2'-O-methoxyethyl (2'-MOE) group, or any modification as disclosed herein. The EONs of the present invention preferably comprise at least one phosphorothioate linkage. 2'-OMe and 2'-MOEs should not influence the location of the stereospecific PS, only global effect on the EON properties may be observed including hydrophobicity, melting temperature, etc. For this, combinations may have an influence. However, for the binding of the deaminase domain, it should not interfere. All mentioned chemical modifications could be applied, in principle, to other disease models, as they involve the backbone not the primary sequence. Calculations should not be systematically repeated with other disease models except if it is shown that affinities can strongly vary between RNA targets. This would suggest that the local binding is shifted.

In one particular embodiment of the present invention, the EON is longer than 10, 11, 12, 13, 14, 15, 16 or 17 nucleotides. Preferably, the EON is shorter than 100 nucleotides, more preferably shorter than 60 nucleotides, and even more preferably, the EON comprises 18 to 70 nucleotides, 18 to 60 nucleotides, or 18 to 50 nucleotides. The invention also relates to a pharmaceutical composition comprising the EON according to the invention, and a pharmaceutically acceptable carrier. The invention also relates to an EON according to the invention for use in the treatment or prevention of a genetic disorder, preferably selected from the group consisting of Cystic fibrosis, Hurler Syndrome, alpha-1-antitrypsin (A1AT) deficiency, Parkinson's disease, Alzheimer's disease, albinism, Amyotrophic lateral sclerosis, Asthma, β-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-eso1 related cancer, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, and cancer. In a particularly preferred embodiment, the EONs according to the invention are for use in the treatment of Cystic Fibrosis and used for the deamination of a target adenosine present in a PTC present in the human CFTR (pre) mRNA. In another aspect the invention relates to a use of an EON according to the invention in the manufacture of a medicament for the treatment or prevention of a disease, preferably Cystic Fibrosis. In yet another embodiment of the invention, it relates to a method for the deamination of at least one target adenosine present in a PTC in a target RNA in a cell, the method comprising the steps of providing the cell with an EON according to the invention; allowing uptake by the cell of the EON; allowing annealing of the EON to the target RNA; allowing an ADAR enzyme comprising a natural dsRNA binding domain as found in the wild type enzyme to deaminate the target adenosine in the target RNA to an inosine; and optionally identifying the presence of the inosine in the targeted RNA, preferably wherein the last step comprises sequencing the targeted RNA sequence; assessing the presence of a functional, elongated, full length and/or wild type protein when the target adenosine is located in a UGA or UAG stop codon, which is edited to a UGG codon through the deamination; assessing the presence of a functional, elongated, full length and/or wild type protein when two target adenosines are located in a UAA stop codon, which is edited to a UGG codon through the deamination of both target adenosines; assessing whether splicing of the pre-mRNA was altered by the deamination; or using a functional read-out, wherein the target RNA after the deamination encodes a functional, full length, elongated and/or wild type protein. In one particularly preferred embodiment, the invention relates to an EON or a method according to the invention, wherein the target RNA sequence encodes CFTR (e.g. to edit a G542X, W1282X, R553X, R1162X, Y122X, W1089X, W846X, W401X, 621+1G>T or 1717-1G>A mutation.

It is an important aspect of the invention that the EON comprises one or more nucleotides with one or more sugar modifications. Thereby, a single nucleotide of the EON can have one, or more than one sugar modification. Within the EON, one or more nucleotide(s) can have such sugar modification(s).

It is also an important aspect of the invention that the nucleotide within the EON of the present invention that is opposite to the nucleotide that needs to be edited does not contain a 2'-O-methyl modification (herein often referred to as a 2'-OMe group, or as 2'-O-methylation) and preferably comprises a 2'—OH group, or is a deoxyribose with a 2'—H group. It is preferred that the nucleotides that are directly 3' and/or 5' of this nucleotide (the 'neighbouring nucleotides') also lack such a chemical modification, although it is believed that it is tolerated that one of these neighbouring nucleotides may contain a 2'-O-alkyl group (such as a 2'-O-methyl group), but preferably not both. Either one, or both neighbouring nucleotides may be 2'-OH or a compatible substitution (as defined herein).

Preferably the EON of the present invention does not have a portion that is complementary to the target RNA or the RNA region that comprises the target adenosine that allows the EON in itself to fold into an intramolecular hairpin or other type of (stem) loop structure (herein also referred to as "auto-looping" or "self-looping"), and which may potentially act as a structure that sequesters ADAR. In one aspect, the single stranded EON of the present invention is fully complementary with the target RNA, although it preferably does not perfectly pair on at least one position, which is at the position of the target adenosine, where the opposite nucleoside is then preferably a cytidine. The single-stranded RNA editing oligonucleotides of the present invention may also have one or more mismatches, wobbles or bulges (no opposite nucleoside) with the target sequence, at other positions than at the target adenosine position. These wobbles, mismatches and/or bulges of the EON of the present invention with the target sequence do not prevent hybridization of the oligonucleotide to the target RNA sequence, but add to the RNA editing efficiency by the ADAR present in the cell, at the target adenosine position. The person skilled in the art is able to determine whether hybridization under physiological conditions still does take place. In contrast to the prior art, the EON of the present invention uses a mammalian ADAR enzyme present in the cell, wherein the ADAR enzyme comprises its natural dsRNA binding domain as found in the wild type enzyme. The EONs according to the present invention can utilise endogenous cellular pathways and naturally available ADAR enzyme, or enzymes with ADAR activity (which may be yet unidentified ADAR-like enzymes) to specifically edit a target adenosine in a target RNA sequence. As disclosed herein, the single-stranded RNA editing-inducing oligonucleotides of the invention are capable of deamination of a specific target adenosine nucleotide in a target RNA sequence. Ideally, only one adenosine is deaminated. Alternatively 1, 2, or 3 adenosine nucleotides are deaminated, but preferably only one. Taking the features of the EONs of the present invention together, there is no need for modified recombinant ADAR expression, there is no need for conjugated entities attached to the EON, or the presence of long recruitment portions that are not complementary to the target RNA sequence. Besides that, the EON of the present invention does allow for the specific deamination of a target adenosine present in the target RNA molecule to an inosine by a natural ADAR enzyme comprising a natural dsRNA binding domain as found in the wild type enzyme, without the risk of promiscuous editing elsewhere in the RNA/EON complex.

Analysis of natural targets of ADAR enzymes indicated that these generally include mismatches between the two strands that form the RNA helix edited by ADAR1 or ADAR2. It has been suggested that these mismatches enhance the specificity of the editing reaction (Stefl et al. 2006. Structure 14 (2): 345-355; Tian et al. 2011. Nucleic Acids Res 39 (13): 5669-5681). Characterization of optimal patterns of paired/mismatched nucleotides between the EONs and the target RNA also appears crucial for development of efficient ADAR-based EON therapy. An improved feature of the EONs of the present invention is the use of specific internucleotide linkage modifications at predefined spots to ensure stability as well as proper ADAR binding and activity.

These changes may vary and may further include modifications in the backbone of the EON, in the sugar moiety of the nucleotides as well as in the nucleobases. They may also be variably distributed throughout the sequence of the EON, depending on the target and on secondary structures. Specific chemical modifications may be needed to support interactions of different amino acid residues within the RNA-binding domains of ADAR enzymes, as well as those in the deaminase domain. For example, stereospecific phosphorothioate configuration modifications, and/or 2'-O-methyl modifications are tolerated in some parts of the EON, while in other parts they should be avoided so as not to disrupt crucial interactions of the enzyme with the phosphate and/or 2'—OH groups. Part of these design rules are guided by the published structures of ADAR2, while others have to be defined empirically. Different preferences may exist for ADAR1 and ADAR2. The modifications should also be selected such that they prevent degradation of the EONs. Specific nucleotide modifications may also be necessary to enhance the editing activity on substrate RNAs where the target sequence is not optimal for ADAR editing. Previous work has established that certain sequence contexts are more amenable to editing. For example, the target sequence 5'-UAG-3' (with the target A in the middle) contains the most preferred nearest-neighbor nucleotides for ADAR2, whereas a 5'-CAA-3' target sequence is disfavored (Schneider et al. 2014. Nucleic Acids Res 42 (10): e87). The recent structural analysis of ADAR2 deaminase domain hints at the possibility of enhancing editing by careful selection of the nucleotides that are opposite to the target trinucleotide. For example, the 5'-CAA-3' target sequence, paired to a 3'-GCU-5' sequence on the opposing strand (with the A-C mismatch formed in the middle in this triplet), is disfavored because the guanosine base sterically clashes with an amino acid side chain of ADAR2. However, here it is postulated that a smaller nucleobase, such as inosine, could potentially fit better into this position without causing steric clashes, while still retaining the base-pairing potential to the opposing cytidine. Modifications that could enhance activity of suboptimal sequences include the use of backbone modifications that increase the flexibility of the EON or, conversely, force it into a conformation that favors editing.

Definitions of Terms as Used Herein

The terms 'adenine', 'guanine', 'cytosine', 'thymine', 'uracil' and 'hypoxanthine' (the nucleobase in inosine) as used herein refer to the nucleobases as such.

The terms 'adenosine', 'guanosine', 'cytidine', 'thymidine', 'uridine' and 'inosine', refer to the nucleobases linked to the (deoxy) ribosyl sugar.

The term 'nucleoside' refers to the nucleobase linked to the (deoxy) ribosyl sugar.

The term 'nucleotide' refers to the respective nucleobase-(deoxy) ribosyl-phospholinker, as well as any chemical modifications of the ribose moiety or the phospho group. Thus the term would include a nucleotide including a locked ribosyl moiety (comprising a 2'-4' bridge, comprising a methylene group or any other group, well known in the art), a nucleotide including a linker comprising a phosphodiester, phosphotriester, phosphoro(di)thioate, methylphosphonates, phosphoramidate linkers, and the like.

Sometimes the terms adenosine and adenine, guanosine and guanine, cytosine and cytidine, uracil and uridine, thymine and thymidine, inosine and hypo-xanthine, are used interchangeably to refer to the corresponding nucleobase, nucleoside or nucleotide.

Sometimes the terms nucleobase, nucleoside and nucleotide are used interchangeably, unless the context clearly requires differently. The terms 'ribonucleoside' and 'deoxyribonucleoside', or 'ribose' and 'deoxyribose' are as used in the art.

Whenever reference is made to an 'oligonucleotide', both oligoribonucleotides and deoxyoligoribonucleotides are meant unless the context dictates otherwise. Whenever reference is made to an 'oligoribonucleotide' it may comprise the bases A, G, C, U or I. Whenever reference is made to a 'deoxyoligoribonucleotide' it may comprise the bases A, G, C, T or I. In a preferred aspect, the EON of the present invention is an oligoribonucleotide that may comprise chemical modifications, and may include deoxynucleotides (DNA) at certain specified positions.

Whenever reference is made to nucleotides in the oligonucleotide construct, such as cytosine, 5-methylcytosine, 5-hydroxymethylcytosine and β-D-Glucosyl-5-hydroxymethylcytosine are included; when reference is made to adenine, N6-Methyladenine and 7-methyladenine are included; when reference is made to uracil, dihydrouracil, 4-thiouracil and 5-hydroxymethyluracil are included; when reference is made to guanine, 1-methylguanine is included.

Whenever reference is made to nucleosides or nucleotides, ribofuranose derivatives, such as 2'-desoxy, 2'-hydroxy, and 2'-O-substituted variants, such as 2'-O-methyl, are included, as well as other modifications, including 2'-4' bridged variants.

Whenever reference is made to oligonucleotides, linkages between two mono-nucleotides may be phosphodiester linkages as well as modifications thereof, including, phosphodiester, phosphotriester, phosphoro(di)thioate, methylphosphonate, phosphor-amidate linkers, and the like.

The term 'comprising' encompasses 'including' as well as 'consisting', e.g. a composition 'comprising X' may consist exclusively of X or may include something additional, e.g. X+Y.

The term 'about' in relation to a numerical value x is optional and means, e.g. x+10%.

The word 'substantially' does not exclude 'completely', e.g. a composition which is 'substantially free from Y' may be completely free from Y. Where relevant, the word 'substantially' may be omitted from the definition of the invention.

The term "complementary" as used herein refers to the fact that the AON (or EON as it is often referred to herein) hybridizes under physiological conditions to the target sequence. The term does not mean that each and every nucleotide in the AON has a perfect pairing with its opposite nucleotide in the target sequence. In other words, while an AON may be complementary to a target sequence, there may be mismatches, wobbles and/or bulges between AON and the target sequence, while under physiological conditions that AON still hybridizes to the target sequence such that the cellular RNA editing enzymes can edit the target adenosine. The term "substantially complementary" therefore also means that in spite of the presence of the mismatches, wobbles, and/or bulges, the AON has enough matching nucleotides between AON and target sequence that under physiological conditions the AON hybridizes to the target RNA. As shown herein, an AON may be complementary, but may also comprise one or more mismatches, wobbles and/or bulges with the target sequence, as long as under physiological conditions the AON is able to hybridize to its target.

The term 'downstream' in relation to a nucleic acid sequence means further along the sequence in the 3' direction; the term 'upstream' means the converse. Thus in any sequence encoding a polypeptide, the start codon is upstream of the stop codon in the sense strand, but is downstream of the stop codon in the antisense strand.

References to 'hybridisation' typically refer to specific hybridisation, and exclude non-specific hybridisation. Specific hybridisation can occur under experimental conditions chosen, using techniques well known in the art, to ensure that the majority of stable interactions between probe and target are where the probe and target have at least 70%, preferably at least 80%, more preferably at least 90% sequence identity.

The term 'mismatch' is used herein to refer to opposing nucleotides in a double stranded RNA complex which do not form perfect base pairs according to the Watson-Crick base pairing rules. Mismatched nucleotides are G-A, C-A, U-C, A-A, G-G, C-C, U-U pairs. In some embodiments EONs of the present invention comprise fewer than four mismatches, for example 0, 1 or 2 mismatches. Wobble base pairs are: G-U, I-U, I-A, and I-C base pairs.

The term 'splice mutation' relates to a mutation in a gene that encodes for a pre-mRNA, wherein the splicing machinery is dysfunctional in the sense that splicing of introns from exons is disturbed and due to the aberrant splicing the subsequent translation is out of frame resulting in premature termination of the encoded protein. Often such shortened proteins are degraded rapidly and do not have any functional activity, as discussed herein. In a preferred aspect, the splice mutations that are targeted by the EONs and through the methods of the present invention are present in the human CFTR gene, more preferably the splice mutations 621+1G>T and 1717-1G>A. The exact mutation does not have to be the target for the RNA editing; it may be that (for instance in the case of 621+1G>T) a neighbouring or nearby adenosine in the splice mutation is the target nucleotide, which conversion to I fixes the splice mutation back to a normal state. The skilled person is aware of methods to determine whether or not normal splicing is restored, after RNA editing of the adenosine within the splice mutation site or area.

An EON according to the present invention may be chemically modified almost in its entirety, for example by providing nucleotides with a 2'-O-methylated sugar moiety (2'-OMe) and/or with a 2'-O-methoxyethyl sugar moiety (2'-MOE). However, the nucleotide opposite the target adenosine does not comprise the 2'-OMe modification, and in yet a further preferred aspect, at least one and in a preferred aspect both the two neighbouring nucleotides flanking each nucleotide opposing the target adenosine further do not comprise a 2'-OMe modification. Complete modification, wherein all nucleotides within the EON holds a 2'-OMe modification results in a non-functional oligonucleotide as far as RNA editing goes, presumably because it hinders the ADAR activity at the targeted position. In general, an adenosine in a target RNA can be protected from editing by providing an opposing nucleotide with a 2'-OMe group, or by providing a guanine or adenine as opposing base, as these two nucleobases are also able to reduce editing of the opposing adenosine.

Various chemistries and modification are known in the field of oligonucleotides that can be readily used in accordance with the invention. The regular internucleosidic linkages between the nucleotides may be altered by mono- or di-thioation of the phosphodiester bonds to yield phosphorothioate esters or phosphorodithioate esters, respectively. Other modifications of the internucleosidic linkages are possible, including amidation and peptide linkers.

The ribose sugar may be modified by substitution of the 2'-O moiety with a lower alkyl (C1-4, such as 2'-O-Me), alkenyl (C2-4), alkynyl (C2-4), methoxyethyl (2'-MOE), or other substituent. Preferred substituents of the 2' OH group are a methyl, methoxyethyl or 3,3'-dimethylallyl group. The latter is known for its property to inhibit nuclease sensitivity due to its bulkiness, while improving efficiency of hybridization (Angus & Sproat FEBS 1993 Vol. 325, no. 1, 2, 123-7). Alternatively, locked nucleic acid sequences (LNAs), comprising a 2'-4' intramolecular bridge (usually a methylene bridge between the 2' oxygen and 4' carbon) linkage inside the ribose ring, may be applied. Purine nucleobases and/or pyrimidine nucleobases may be modified to alter their properties, for example by amination or deamination of the heterocyclic rings. The exact chemistries and formats may depend from oligonucleotide construct to oligonucleotide construct and from application to application, and may be worked out in accordance with the wishes and preferences of those of skill in the art.

The EON according to the invention should normally be longer than 10 nucleotides, preferably more than 11, 12, 13, 14, 15, 16, still more preferably more than 17 nucleotides. In one embodiment the EON according to the invention is longer than 20 nucleotides. The oligonucleotide according to the invention is preferably shorter than 100 nucleotides, still more preferably shorter than 60 nucleotides. In one embodiment the EON according to the invention is shorter than 50 nucleotides. In a preferred aspect, the oligonucleotide according to the invention comprises 18 to 70 nucleotides, more preferably comprises 18 to 60 nucleotides, and even more preferably comprises 18 to 50 nucleotides. Hence, in a most preferred aspect, the oligonucleotide of the present invention comprises 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides.

It is known in the art, that RNA editing entities (such as human ADAR enzymes) edit dsRNA structures with varying specificity, depending on a number of factors. One important factor is the degree of complementarity of the two strands making up the dsRNA sequence. Perfect complementarity of the two strands usually causes the catalytic domain of hADAR to deaminate adenosines in a non-discriminative manner, reacting more or less with any adenosine it encounters. The specificity of hADAR1 and 2 can be increased by introducing chemical modifications and/or ensuring a number of mismatches in the dsRNA, which presumably help to position the dsRNA binding domains in a way that has not been clearly defined yet. Additionally, the deamination reaction itself can be enhanced by providing an EON that comprises a mismatch opposite the adenosine to be edited. The mismatch is preferably created by providing a targeting portion having a cytidine opposite the adenosine to be edited. As an alternative, also uridines may be used opposite the adenosine, which, understandably, will not result in a 'mismatch' because U and A pair. Upon deamination of the adenosine in the target strand, the target strand will obtain an inosine which, for most biochemical processes, is "read" by the cell's biochemical machinery as a G. Hence, after A to I conversion, the mismatch has been resolved, because I is perfectly capable of base pairing with the opposite C in the targeting portion of the oligonucleotide construct according to the invention. After the mismatch has been resolved due to editing, the substrate is released and the oligonucleotide construct-editing entity complex is released from the target RNA sequence, which then becomes available for downstream biochemical processes, such as splicing and translation. Also this on/off rate is important because the targeting oligonucleotide should not be too tightly bound to the target RNA.

The desired level of specificity of editing the target RNA sequence may depend from target to target. Following the instructions in the present patent application, those of skill in the art will be capable of designing the complementary portion of the oligonucleotide according to their needs, and, with some trial and error, obtain the desired result.

The oligonucleotide of the invention will usually comprise the normal nucleotides A, G, U and C, but may also include inosine (I), for example instead of one or more G nucleotides.

To prevent undesired editing of adenosines in the target RNA sequence in the region of overlap with the oligonucleotide construct, the oligonucleotide may be chemically modified. It has been shown in the art, that 2'-O-methylation of the ribosyl-moiety of a nucleoside opposite an adenosine in the target RNA sequence dramatically reduces deamination of that adenosine by ADAR (Vogel et al. 2014). Hence, by including 2'-O-methyl (2'-OMe) nucleotides in desired position of the oligonucleotide construct, the specificity of editing is dramatically improved. Other 2'-O substitutions of the ribosyl moiety, such as 2'-O-methoxyethyl (2'-MOE) and 2'-O-dimethylallyl groups may also reduce unwanted editing of the corresponding (opposite) adenosine in the target RNA sequence. All these modifications may be applied in the oligonucleotides of the present invention. Other chemical modifications are also readily available to the person having ordinary skill in the art of oligonucleotide synthesis and design. The synthesis of such chemically modified oligonucleotides and testing them in methods according to the invention does not pose an undue burden and other modifications are encompassed by the present invention.

RNA editing molecules present in the cell will usually be proteinaceous in nature, such as the ADAR enzymes found in metazoans, including mammals. Preferably, the cellular editing entity is an enzyme, more preferably an adenosine deaminase or a cytidine deaminase, still more preferably an adenosine deaminase. These are enzymes with ADAR activity. The ones of most interest are the human ADARs, hADAR1 and hADAR2, including any isoforms thereof such as hADAR1 p110 and p150. RNA editing enzymes known in the art, for which oligonucleotide constructs according to the invention may conveniently be designed, include the adenosine deaminases acting on RNA (ADARs), such as hADAR1 and hADAR2 in humans or human cells and cytidine deaminases. Human ADAR3 (hADAR3) has been described in the prior art, but reportedly has no deaminase activity. It is known that hADAR1 exists in two isoforms; a long 150 kDa interferon inducible version and a shorter, 100 kDa version, that is produced through alternative splicing from a common pre-mRNA. Consequently, the level of the 150 kDa isoform present in the cell may be influenced by interferon, particularly interferon-gamma (IFN-gamma). hADAR1 is also inducible by TNF-alpha. This provides an opportunity to develop combination therapy, whereby interferon-gamma or TNF-alpha and oligonucleotides according to the invention are administered to a patient either as a combination product, or as separate products, either simultaneously or subsequently, in any order. Certain disease conditions may already coincide with increased IFN-gamma or TNF-alpha levels in certain tissues of a patient, creating further opportunities to make editing more specific for diseased tissues.

Examples of chemical modifications in the EONs of the present invention are modifications of the sugar moiety, including by cross-linking substituents within the sugar (ribose) moiety (e.g. as in LNA or locked nucleic acids), by substitution of the 2'-O atom with alkyl (e.g. 2'-O-methyl), alkynyl (2'-O-alkynyl), alkenyl (2'-O-alkenyl), alkoxyalkyl (e.g. methoxyethyl, 2'-MOE) groups, having a length as specified above, and the like. In addition, the phosphodiester group of the backbone may be modified by thioation, dithioation, amidation and the like to yield phosphorothioate, phosphorodithioate, phosphoramidate, etc., internucleosidic linkages. The internucleosidic linkages may be replaced in full or in part by peptidic linkages to yield in peptidonucleic acid sequences and the like. Alternatively, or in addition, the nucleobases may be modified by (de) amination, to yield inosine or 2'6'-diaminopurines and the like. A further modification may be methylation of the C5 in the cytidine moiety of the nucleotide, to reduce potential immunogenic properties known to be associated with CpG sequences.

In case the dsRNA complex recruits ADAR enzymes to deaminate an A to I in the target RNA sequence, the base-pair, mismatch, bulge or wobble between the adenosine to be edited and the opposite nucleotide may comprise an adenosine, a guanine, a uridine or a cytidine residue, but preferably a cytidine residue. Except for the potential mismatch opposite the editing site (when no uridine is applied), the remaining portion of the EON may be perfectly complementary to the target RNA. However, as shown herein, in certain aspects the invention relates to EONs that comprise a limited number of imperfect matches. It will be understood by a person having ordinary skill in the art that the extent to which the editing entities inside the cell are redirected to other target sites may be regulated by varying the affinity of the oligonucleotides according to the invention for the recognition domain of the editing molecule. The exact modification may be determined through some trial and error and/or through computational methods based on structural interactions between the oligonucleotide and the recognition domain of the editing molecule.

In addition, or alternatively, the degree of recruiting and redirecting the editing entity resident in the cell may be regulated by the dosing and the dosing regimen of the oligonucleotide. This is something to be determined by the experimenter (in vitro) or the clinician, usually in phase I and/or II clinical trials.

The invention concerns the modification of target RNA sequences in eukaryotic, preferably metazoan, more preferably mammalian cells. In principle the invention can be used with cells from any mammalian species, but it is preferably used with a human cell. The invention can be used with cells from any organ e.g. skin, lung, heart, kidney, liver, pancreas, gut, muscle, gland, eye, brain, blood and the like. The invention is particularly suitable for modifying sequences in cells, tissues or organs implicated in a diseased state of a (human) subject, for instance when the human subject suffers from Cystic Fibrosis. Such cells include but are not limited to epithelial cells of the lung. The cell can be located in vitro or in vivo. One advantage of the invention is that it can be used with cells in situ in a living organism, but it can also be used with cells in culture. In some embodiments cells are treated ex vivo and are then introduced into a living organism (e.g. re-introduced into an organism from whom they were originally derived). The invention can also be used to edit target RNA sequences in cells within a so-called organoid. Organoids can be thought of as three-dimensional in vitro-derived tissues but are driven using specific conditions to generate individual, isolated tissues (e.g. see Lancaster & Knoblich, Science 2014, vol. 345 no. 6194 1247125). In a therapeutic setting they are useful because they can be derived in vitro from a patient's cells, and the organoids can then be re-introduced to the patient as autologous material which is less likely to be rejected than a normal transplant. The cell to be treated will generally have a genetic mutation. The mutation may be heterozygous or homozygous. The invention will typically be used to modify point mutations, such as N to A mutations, wherein N may be G, C, U (on the DNA level T), preferably G to A mutations, or N to C mutations, wherein N may be A, G, U (on the DNA level T), preferably U to C mutations.

Without wishing to be bound be theory, the RNA editing through hADAR1 and hADAR2 is thought to take place on primary transcripts in the nucleus, during transcription or splicing, or in the cytoplasm, where e.g. mature mRNA, miRNA or ncRNA can be edited. Different isoforms of the editing enzymes are known to localize differentially, e.g. with hADAR1 p110 found mostly in the nucleus, and hADAR1 p150 in the cytoplasm. The RNA editing by cytidine deaminases is thought to take place on the mRNA level.

The invention is used to make a change in a target RNA sequence in a eukaryotic cell through the use of an oligonucleotide that is capable of targeting a site to be edited and recruiting RNA editing entities resident in the cell to bring about the editing reaction(s). Preferred editing reactions are adenosine deaminations, converting adenosines into inosines. The target RNA sequence may comprise a mutation that one may wish to correct or alter, such as a point mutation (a transition or a transversion). The target RNA may be any cellular or viral RNA sequence, but is more usually a pre-mRNA or an mRNA with a protein coding function.

Many genetic diseases are caused by G to A mutations, and these are preferred target diseases because adenosine deamination at the mutated target adenosine will reverse the mutation to a codon giving rise to a functional, full length and/or wild type protein, especially when it concerns PTCs. Preferred examples of genetic diseases that can be prevented and/or treated with oligonucleotides according to the invention are any disease where the modification of one or more adenosines in a target RNA will bring about a (potentially) beneficial change. Especially preferred is Cystic Fibrosis, and more specifically the RNA editing of adenosines in the disease-inducing PTCs in CFTR RNA is preferred. Those skilled in the art of CF mutations recognise that between 1000 and 2000 mutations are known in the CFTR gene, including G542X, W1282X, R553X, R1162X, Y122X, W1089X, W846X, W401X, 621+1G>T or 1717-1G>A.

The target sequence is endogenous to the eukaryotic, preferably mammalian, more preferably human cell.

The amount of oligonucleotide to be administered, the dosage and the dosing regimen can vary from cell type to cell type, the disease to be treated, the target population, the mode of administration (e.g. systemic versus local), the severity of disease and the acceptable level of side activity, but these can and should be assessed by trial and error during in vitro research, in pre-clinical and clinical trials. The trials are particularly straightforward when the modified sequence leads to an easily-detected phenotypic change. It is possible that higher doses of oligonucleotide could compete for binding to a nucleic acid editing entity (e.g. ADAR) within a cell, thereby depleting the amount of the entity which is free to take part in RNA editing, but routine dosing trials will reveal any such effects for a given oligonucleotide and a given target.

One suitable trial technique involves delivering the oligonucleotide construct to cell lines, or a test organism and then taking biopsy samples at various time points thereafter. The sequence of the target RNA can be assessed in the biopsy sample and the proportion of cells having the modification can easily be followed. After this trial has been performed once then the knowledge can be retained and future delivery can be performed without needing to take biopsy samples. A method of the invention can thus include a step of identifying the presence of the desired change in the cell's target RNA sequence, thereby verifying that the target RNA sequence has been modified. This step will typically involve sequencing of the relevant part of the target RNA, or a cDNA copy thereof (or a cDNA copy of a splicing product thereof, in case the target RNA is a pre-mRNA), as discussed above, and the sequence change can thus be easily verified. Alternatively the change may be assessed on the level of the protein (length, glycosylation, function or the like), or by some functional read-out, such as a (n) (inducible) current, when the protein encoded by the target RNA sequence is an ion channel, for example. In the case of CFTR function, an Ussing chamber assay or an NPD test in a mammal, including humans, are well known to a person skilled in the art to assess restoration or gain of function.

After RNA editing has occurred in a cell, the modified RNA can become diluted over time, for example due to cell division, limited half-life of the edited RNAs, etc. Thus, in practical therapeutic terms a method of the invention may involve repeated delivery of an oligonucleotide construct until enough target RNAs have been modified to provide a tangible benefit to the patient and/or to maintain the benefits over time.

Oligonucleotides of the invention are particularly suitable for therapeutic use, and so the invention provides a pharmaceutical composition comprising an oligonucleotide of the invention and a pharmaceutically acceptable carrier. In some embodiments of the invention the pharmaceutically acceptable carrier can simply be a saline solution. This can usefully be isotonic or hypotonic, particularly for pulmonary delivery. The invention also provides a delivery device (e.g. syringe, inhaler, nebuliser) which includes a pharmaceutical composition of the invention.

The invention also provides an oligonucleotide of the invention for use in a method for making a change in a target RNA sequence in a mammalian, preferably human cell, as described herein. Similarly, the invention provides the use of an oligonucleotide construct of the invention in the manufacture of a medicament for making a change in a target RNA sequence in a mammalian, preferably human cell, as described herein.

The invention also relates to a method for the deamination of at least one specific target adenosine present in a target RNA sequence in a cell, the method comprising the steps of: providing the cell with an EON according to the invention; allowing uptake by the cell of the EON; allowing annealing of the EON to the target RNA sequence; allowing a mammalian ADAR enzyme comprising a natural dsRNA binding domain as found in the wild type enzyme to deaminate the target adenosine in the target RNA sequence to an inosine; and optionally identifying the presence of the inosine in the RNA sequence.

Introduction of the EON according to the present invention into the cell is performed by general methods known to the person skilled in the art. After deamination the read-out of the effect (alteration of the target RNA sequence) can be monitored through different ways. Hence, the identification step of whether the desired deamination of the target adenosine has indeed taken place depends generally on the position of the target adenosine in the target RNA sequence, and the effect that is incurred by the presence of the adenosine (point mutation, early stop codon). Hence, in a preferred aspect, depending on the ultimate deamination effect of A to I conversion, the identification step comprises: sequencing the target RNA; assessing the presence of a functional, elongated, full length and/or wild type protein; assessing whether splicing of the pre-mRNA was altered by the deamination; or using a functional read-out, wherein the target RNA after the deamination encodes a functional, full length, elongated and/or wild type protein. In the event that there is a UAA stop codon it means that both adenosines need to be deaminated. Hence, the invention also relates to oligonucleotides and methods wherein two adenosines that are next to each other are co-deaminated by an RNA editing enzyme such as ADAR. In this particular case, the UAA stop codon is converted into a UGG Trp-encoding codon. Because the deamination of the adenosine to an inosine may result in a protein that is no longer suffering from the mutated A at the target position, the identification of the deamination into inosine may also be a functional read-out, for instance an assessment on whether a functional protein is present, or even the assessment that a disease that is caused by the presence of the adenosine is (partly) reversed. The functional assessment for each of the diseases mentioned herein will generally be according to methods known to the skilled person. A very suitable manner to identify the presence of an inosine after deamination of the target adenosine is of course RT-PCR and sequencing, using methods that are well-known to the person skilled in the art.

The oligonucleotide according to the invention is suitably administrated in aqueous solution, e.g. saline, or in suspension, optionally comprising additives, excipients and other ingredients, compatible with pharmaceutical use, at concentrations ranging from 1 ng/ml to 1 g/ml, preferably from 10 ng/ml to 500 mg/ml, more preferably from 100 ng/ml to 100 mg/ml. Dosage may suitably range from between about 1 µg/kg to about 100 mg/kg, preferably from about 10 µg/kg to about 10 mg/kg, more preferably from about 100 µg/kg to about 1 mg/kg. Administration may be by inhalation (e.g. through nebulization), intranasally, orally, by injection or infusion, intravenously, subcutaneously, intra-dermally, intra-cranially, intramuscularly, intra-tracheally, intra-peritoneally, intra-rectally, and the like. Administration may be in solid form, in the form of a powder, a pill, or in any other form compatible with pharmaceutical use in humans. The invention is particularly suitable for treating genetic diseases, such as cystic fibrosis.

In some embodiments the oligonucleotide construct can be delivered systemically, but it is more typical to deliver an oligonucleotide to cells in which the target sequence's phenotype is seen. For instance, mutations in CFTR cause cystic fibrosis which is primarily seen in lung epithelial tissue, so with a CFTR target sequence it is preferred to deliver the oligonucleotide construct specifically and directly to the lungs. This can be conveniently achieved by inhalation e.g. of a powder or aerosol, typically via the use of a nebuliser. Especially preferred are nebulizers that use a so-called vibrating mesh, including the PARI eFlow (Rapid) or the i-neb from Respironics. It is to be expected that inhaled delivery of oligonucleotide constructs according to the invention can also target these cells efficiently, which in the case of CFTR gene targeting could lead to amelioration of gastrointestinal symptoms also associated with cystic fibrosis. In some diseases the mucus layer shows an increased thickness, leading to a decreased absorption of medicines via the lung. One such a disease is chronical bronchitis, another example is cystic fibrosis. Various forms of mucus normalizers are available, such as DNases, hypertonic saline or mannitol, which is commercially available under the name of Bronchitol. When mucus normalizers are used in combination with RNA editing oligonucleotide constructs, such as the oligonucleotide constructs according to the invention, they might increase the effectiveness of those medicines. Accordingly, administration of an oligonucleotide construct according to the invention to a subject, preferably a human subject is preferably combined with mucus normalizers, preferably those mucus normalizers described herein. In addition, administration of the oligonucleotide constructs according to the invention can be combined with administration of small molecule for treatment of CF, such as potentiator compounds for example Kalydeco (ivacaftor; VX-770), or corrector compounds, for example VX-809 (lumacaftor) and/or VX-661. Other combination therapies in CF may comprise the use of an oligonucleotide construct according to the invention in combination with an inducer of adenosine deaminase, using IFN-gamma or TNF-alpha. Alternatively, or in combination with the mucus normalizers, delivery in mucus penetrating particles or nanoparticles can be applied for efficient delivery of RNA editing molecules to epithelial cells of for example lung and intestine. Accordingly, administration of an oligonucleotide construct according to the invention to a subject, preferably a human subject, preferably uses delivery in mucus penetrating particles or nanoparticles. Chronic and acute lung infections are often present in patients with diseases such as cystic fibrosis. Antibiotic treatments reduce bacterial infections and the symptoms of those such as mucus thickening and/or biofilm formation. The use of antibiotics in combination with oligonucleotide constructs according to the invention could increase effectiveness of the RNA editing due to easier access of the target cells for the oligonucleotide construct. Accordingly, administration of an oligonucleotide construct according to the invention to a subject, preferably a human subject, is preferably combined with antibiotic treatment to reduce bacterial infections and the symptoms of those such as mucus thickening and/or biofilm formation. The antibiotics can be administered systemically or locally or both. For application in cystic fibrosis patients the oligonucleotide constructs according to the invention, or packaged or complexed oligonucleotide constructs according to the invention may be combined with any mucus normalizer such as a DNase, mannitol, hypertonic saline and/or antibiotics and/or a small molecule for treatment of CF, such as potentiator compounds for example ivacaftor, or corrector compounds, for example lumacaftor and/or VX-661. To increase access to the target cells, Broncheo-Alveolar Lavage (BAL) could be applied to clean the lungs before administration of the oligonucleotide according to the invention.

EXAMPLES

Example 1: Design of Single-Stranded Antisense Editing Oligonucleotides Based on Computational Modeling The inventors of the present invention envisioned that modeling data could possibly support the identification of structural features that could be incorporated into editing oligonucleotides (EONs) to improve (or to increase the efficiency of) editing of target RNA. The suboptimal sequence context was addressed by chemically modifying the nucleotides of the EONs so as to avoid steric hindrances with ADAR, and even to provide a more efficient recruitment of the protein. To guide this process, the existing RNA-bound ADAR2 structures were used as a starting point (the structural template). The published structure of the ADAR2 deaminase domain in interaction with a double-stranded RNA (Matthews et al., Nature Structural and Molecular Biology, 2016) was analysed and a network of intra and intermolecular distances required for new structure calculations was generated. For the intra and intermolecular distance values, upper limits were defined. For intramolecular distances, upper limits correspond to distances observed in the RNA-bound ADAR2 deaminase X-ray structure. For intermolecular distances, upper limits were set between 1 to 3 Å above the observed distances allowing side-chains adaptation in the binding interface. For secondary structure elements of the ADAR2 deaminase domain, upper and lower distance limits were inserted to characterize the hydrogen-bonds network classically detected in a-helices and B-sheets. Dihedral angle constraints were derived from the published structure. This approach is based on standard methods used to solve protein-RNA structures in solution (Nuclear Magnetic Resonance Spectroscopy) that are known to the person skilled in the art, and integrates torsion angle as well as molecular dynamics steps. Structures of the ADAR2 deaminase domain bound to functionally optimized EONs were calculated with CYANA3.97 (Herrmann et al., J. Mol. Biol., 2002) and selected atomic models were refined with the SANDER module of AMBER16 (Case D. A. et al., J. Comput. Chem., 2005) by simulated annealing in implicit water using the ff99SB force field. In silico, a double-stranded RNA complex composed of EONs annealed to the Idua RNA target was used. This protocol enabled the investigation of the atomic details of the interaction between the protein side-chains and the double-stranded RNA-EON helix. The interaction was modulated by chemical modifications of the oxygen-phosphate backbone of the EON.

Example 2: Use of in Silico Modelled EONs in RNA Editing

As outlined above, a pattern of allowable and non-allowable stereospecific phosphorothioate configuration modifications was determined and to further substantiate this in an RNA editing experiment, an enzymatic assay is performed to validate the method experimentally. The procedure of these Hurler syndrome model experiments is as described in WO 2017/220751. In a first experiment, a number of EONs carrying modifications at various positions are tested. In a second experiment, stereospecific phosphorothioate Rp and/or Sp modifications are integrated at specific positions in the EONs in agreement with the atomic scale modelling results as outlined herein. After transfection of the oligonucleotides in MEF cells overexpressing an altered Idua gene with a premature termination codon (W392X), the α-L-iduronidase (the protein encoded by the Idua gene) enzymatic activity is quantified relative to multiple controls. Binding of EONs to their RNA target and subsequent editing by ADAR restore the enzyme function.

The invention claimed is:

1. An oligonucleotide composition comprising an oligonucleotide capable of forming a double stranded complex with a target nucleic acid molecule in a cell, and capable of recruiting an eukaryotic adenosine deaminase enzyme, wherein the target nucleic acid molecule comprises a target adenosine for deamination by the enzyme, wherein the oligonucleotide comprises a nucleotide referred to as nucleotide position 0, which is opposite the target adenosine and which is a cytidine, a deoxycytidine, a uridine, or a deoxyuridine, wherein the internucleotide linkage numbering is such that linkage number 0 is the linkage 5' from nucleotide position 0, and wherein the nucleotide positions and the linkage positions in the oligonucleotide are both positively (+) and negatively (−) incremented towards the 5' and 3' ends, respectively, wherein the oligonucleotide comprises at least one internucleotide linkage which is predominantly an Rp or an Sp stereospecific configuration according to Formula

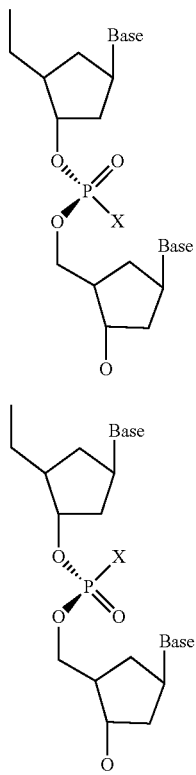

wherein X is —S⁻, —Se⁻, or —BH₃⁻, wherein the oligonucleotide is at least 13, 14, 15, 16 or 17 nucleotides in length, wherein the at least one internucleotide linkage with predominantly an Rp configuration is at linkage position +4, −1, −3, and/or −6, and wherein the at least one internucleotide linkage with predominantly an Sp configuration is at linkage position +10.

2. The oligonucleotide composition of claim 1, wherein the oligonucleotide comprises at least one internucleotide linkage that is an unmodified phosphodiester.

3. The oligonucleotide composition of claim 2, wherein the at least one internucleotide linkage that is an unmodified phosphodiester is at linkage position +5, +6, +7, +8, −4, and/or −5.

4. The oligonucleotide composition of claim 1, wherein the oligonucleotide comprises one or more nucleotides comprising a 2'-O-methoxyethyl (2'-MOE) ribose modification and one or more nucleotides not comprising a 2'-MOE ribose modification.

5. The oligonucleotide composition of claim 1, wherein the oligonucleotide comprises 2'-O-methyl (2'-OMe) ribose modifications at the positions that do not comprise a 2'-MOE ribose modification, or wherein the oligonucleotide comprises deoxynucleotides at positions that do not comprise a 2'-MOE ribose modification.

6. The oligonucleotide composition of claim 1, wherein the eukaryotic adenosine deaminase enzyme is a naturally expressed eukaryotic adenosine deaminase enzyme.

7. The oligonucleotide composition of claim 1, wherein the oligonucleotide is shorter than 100 nucleotides.

8. The oligonucleotide composition of claim 1, wherein the target adenosine is located in a UGA or UAG stop codon, which is edited to a codon encoding tryptophan.

9. A pharmaceutical composition comprising the oligonucleotide composition of claim 1, and a pharmaceutically acceptable carrier.

10. A method for the deamination of at least one target adenosine present in a target nucleic acid molecule in a cell, the method comprising providing the cell with the oligonucleotide composition of claim 1.

11. The method of claim 10, further comprising:
a) sequencing a region of the target nucleic acid molecule, wherein the region comprises the deaminated target adenosine;
b) assessing the presence of a functional, elongated, full length and/or wild type protein when the target adenosine is located in a UGA or UAG stop codon, which is edited to a codon encoding tryptophan through the deamination;
c) assessing the presence of a functional, elongated, full length and/or wild type protein when two target adenosines are located in a UAA stop codon, which is edited to a codon encoding tryptophan through the deamination of both target adenosines;
d) assessing, when the target nucleic acid is pre-mRNA, whether splicing of the pre-mRNA was altered by the deamination; or,
e) when the target nucleic acid after the deamination encodes a functional full length, elongated and/or wild type protein, assessing a function of the protein.

12. The oligonucleotide composition of claim 1, wherein the eukaryotic adenosine deaminase enzyme is ADAR2.

13. The oligonucleotide composition of claim 7, wherein the oligonucleotide is shorter than 60 nucleotides.

14. The method of claim 10, further comprising identifying the presence of the deaminated target adenosine in the target nucleic acid molecule.

* * * * *